(12) United States Patent
Wang et al.

(10) Patent No.: US 6,677,442 B1
(45) Date of Patent: Jan. 13, 2004

(54) NUCLEIC ACID ENCODING HUMAN REV1 PROTEIN

(75) Inventors: Zhigang Wang, Lexington, KY (US); Wensheng Winston Lin, Lexington, KY (US); Hua Xin, Salt Lake City, UT (US); Xiaohua Wu, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 138 days.

(21) Appl. No.: 09/698,286

(22) Filed: Oct. 30, 2000

Related U.S. Application Data

(60) Provisional application No. 60/162,140, filed on Oct. 29, 1999.

(51) Int. Cl.[7] .................. C12N 15/52; C12N 15/63; C12N 5/10
(52) U.S. Cl. .............. 536/23.2; 435/71.1; 435/71.2; 435/325; 435/320.1; 435/252.3; 435/254.11; 435/471; 930/240
(58) Field of Search ................. 536/23.1, 23.2, 536/23.5, 24.3, 24.31; 530/350; 935/71.1, 71.2, 69.1, 325, 320.1, 252.3, 254.11, 410, 471; 930/240

(56) References Cited

FOREIGN PATENT DOCUMENTS

WO        WO99/36550    *  7/1999

OTHER PUBLICATIONS

Mikayama et al. Proc. Natl. Acad Sci. USA vol. 90, pp. 10058–10060, 1993.*
Voet et al. Biochemistry John Wiley & Sons, Inc. pp. 126–128 and 228–234, 1990.*
Larimer et al. J. of Bacteriology vol. 171, No. 1, pp. 230–237, Jan. 1989.*
Wixler et al. FEBS Letters 445 pp. 351–355, 1999.*

* cited by examiner

Primary Examiner—Prema Mertz
(74) Attorney, Agent, or Firm—McDermott, Will & Emery

(57) ABSTRACT

The present invention relates to a human cDNA homologous to the yeast REV1 gene. The sequence of human REV1 (hREV1) gene is described.

7 Claims, 7 Drawing Sheets

```
                                BRCT domain
ceRev1  255 IMEGFSVFVNGYTDPP(6)LMISHGG(4)YYQHGITSYTIASSIA(11)IFIKADWITESIAAGKPLDYRDFLI( 38)
atRev1   87 IFQGVSIFVDGETIPS(6)RITCCET(6)YLCQQTSGLSHLTPQM(11)GYSEAFEGSSIRADDSEEARDHIDD( 88)
scRev1  165 IFKNCVIYINGYTKPG(6)MIVLHGG(4)YLSSKKTVTHIVASNL(11)KVVSPDWIVDSVKEARLLPWQNYSL( 62)
spRev1   63 LFHGLAIAINGYTKPS(6)MIVSNGG(4)YVDGKTSISYLVCSFI(11)KVVKPEWIVDCIKQKKILPWINYRT( 80)
hREV1    48 IFSGVAIYVNGYTDPS(6)LMMLHGG(4)YYSRSKT-THIIATNL(11)KVIRPEWIVESIKAGRLLSYIPYQL(213)
consensus   ++++ +++++G+T P+   +++ +++   Y    + ++ + +    +++ ++++++++++  + +   + +
                        I                              II
ceRev1  377 RNPNEIRDYYARSRLHLISTLAQDMKDFVANL(31)VFHVD---LDCFFVSVAVRNRI------DLKHKEVAITH( 7)
atRev1  261 EDPNEVENYFKNSRLHFIGTWR---NRYRKRF(30)LFESVKYFQDCFFVSVVIKNRL------ELHDKPVAVCH( 5)
scRev1  311 DDPDFLTSYFAHSRLHHLSAWK---ANLKDKF(18)IFHID---FDCFFATVAYLCRSSSFSACDFKRDPIVVCH( 2)
spRev1  227 QNQDFLENFFSSSRLHHLSTWK---ADFKNEI(23)LLHVD---FDCFFASVSTRFSH------ELRLKPVAVAH( 2)
hREV1   344 SDCNEISNFYSHSRLHHISMWKCELTEFVNTL(43)IMHVD---MDCFFVSVGIRNRP------DLKGKPVAVTS(55)
Consensus   ++++F+ ++++ SRLH ++ ++    ++   +    +++++   +DCFF++V+ +++       +++ +++++ +
                    III                                IV
ceRev1  496 SMSEVASCSYAARDCGVKNGMLVRDALQKCPQ---LTLLPYQFEDYVQV(17)VSCDEMYIN(15)LAEHIRKVIREKT
atRev1  377 GTAEISSANYPARAYGVKAGMFVRHAKDLCPQ---LVIVPYNFEAYEEA( 0)LSCDEAFLD(11)LASTIRNEILETT
scRev1  415 KNSDIASCNYVARSYGIKNGMVVSQAEKMLPNGIKLISLPYTFEQFQLK(19)ISIDEAVCV(16)LCEEIRQEIFQGT
spRev1  310 KNSEIASCNYEARKFGIKNGMYVGTAKNLCPS---LRVVDYDFGAYESV(18)ISIDEALLD(13)IAESIRSQVREKT
hREV1   523 SRAEIASCSYEARQLGIKNGMFFGHAKQLCPN---LQAVPYDFHAYKEV(17)VSCDEALVD(14)FANAVRMEIKDQT
Consensus   +  ++++S++Y AR+  G+K+GM++   A++++P+   L   ++Y+F++++ +    +S+DE++++      +++ +R+++ + T
                      V
ceRev1  595 Q-CFASVGIGISTSLLARLATRHAKPDGV-FWVNAHKKNEFISEEKVKDLPGFGYEMMNRLTS 636
atRev1  455 G-CSASVGIGGTMLYARLATRVAKPAGQ-LYISAEKVEEFLDQLPVGTLPGVGSVLKEKLVK 496
scRev1  521 NGCTVSIGCSDSLVLARLALKMAKPNGYNITFKSNLSEEFWSSFKLDDLPGVGHSTLSRLES 563
spRev1  412 N-CEVSVGIGPNVLLARLALRKAKPHNV-YSLSIENVFDVLSPLSVQDLPGVGCSSQAQKLFN 469
hREV1   621 K-CAASVGIGSNILLARMATRKAKPDGQ-YHLKPEEVDDEIRGQLVTNLPGVGHSMESKLAS 662
Consensus   + C +S+G++++++++AR+A + AKP +  +  ++ ++    ++++     + +LPG+G + ++L +
```

Fig. 3

A
5'-*CGCGCGGCCTCCGGTTA (SEQ ID NO:36)
3'-GCGCGCCGGAGGCCAATXACGTACGGTAGG (SEQ ID NO:37)
X = U (-UDG treatment) or AP site (+UDG treatment)
B
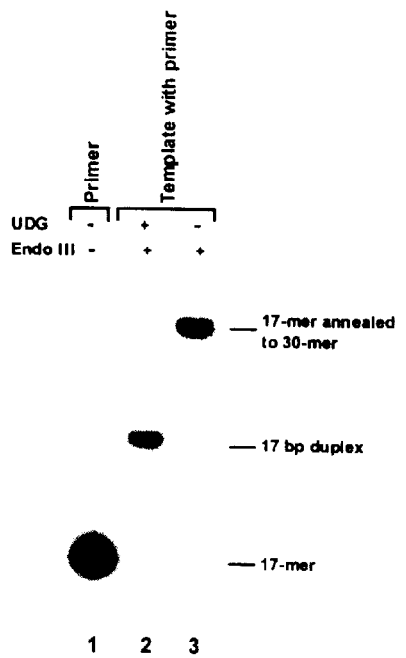
C
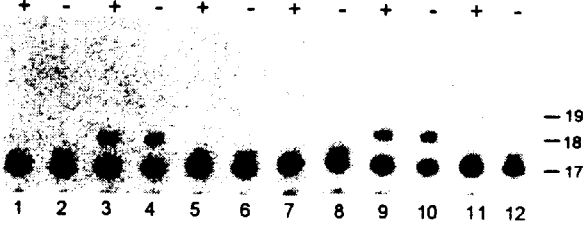
Fig. 6

SEQUENCE LISTING

<160> NUMBER OF SEQ ID NOS: 39

<210> SEQ ID NO 1
<211> LENGTH: 59
<212> TYPE: DNA
<213> ORGANISM: Artificial Sequence
<220> FEATURE:
<223> OTHER INFORMATION: Unknown Organism.  Sequence derived from human
      EST sequence (GenBank accession number AA029147)

<400> SEQUENCE: 1
catggtacga aagcctgggg tcctgtagaa actgcaaaat ttggaggcca tggaatttg         59

<210> SEQ ID NO 2
<211> LENGTH: 22
<212> TYPE: DNA
<213> ORGANISM: Artificial Sequence
<220> FEATURE:
<223> OTHER INFORMATION: Unknown Organism. Sequence derived from Lambda
      bacteriaphage.

<400> SEQUENCE: 2
cggcagtaca atggatttcc tt                                                 22

<210> SEQ ID NO 3
<211> LENGTH: 18
<212> TYPE: DNA
<213> ORGANISM: Artificial Sequence
<220> FEATURE:
<223> OTHER INFORMATION: Unknown Organism. Sequence derived from Lambda
      bacteriaphage.

<400> SEQUENCE: 3
catcgccatc tgctgcac                                                      18

<210> SEQ ID NO 4
<211> LENGTH: 59
<212> TYPE: DNA
<213> ORGANISM: Artificial Sequence
<220> FEATURE:
<223> OTHER INFORMATION: Unknown Organism. Sequence derived from homo
      sapien bone marrow and leukocyte cDNA libraries

<400> SEQUENCE: 4
cattagtttt ctcaatctca gcggaagatc tgtgtatcca ttaacataga tggcaactc         59

<210> SEQ ID NO 5
<211> LENGTH: 59
<212> TYPE: DNA
<213> ORGANISM: Artificial Sequence
<220> FEATURE:
<223> OTHER INFORMATION: Unknown Organism. Sequence derived from homo
      sapien bone marrow and leukocyte cDNA libraries

<400> SEQUENCE: 5 ccacccatg ttttccagcc atcattttca gctcgcttcc tccatccacc tcgcctcat          59

<210> SEQ ID NO 6
<211> LENGTH: 21
<212> TYPE: DNA
<213> ORGANISM: Artificial Sequence
<220> FEATURE:
<223> OTHER INFORMATION: Unknown Organism. Sequence derived from various
      homo sapien tissues

<400> SEQUENCE: 6

-continued

```
cccaggagga ggataaggct g                                                  21
```

<210> SEQ ID NO 7
<211> LENGTH: 29
<212> TYPE: DNA
<213> ORGANISM: Artificial Sequence
<220> FEATURE:
<223> OTHER INFORMATION: Unknown Organsim. Sequence derived from various
      homo sapien tissues

<400> SEQUENCE: 7

```
gtctttgtag ggtattgaca aactcagtc                                          29
```

<210> SEQ ID NO 8
<211> LENGTH: 4255
<212> TYPE: DNA
<213> ORGANISM: Homo sapiens

<400> SEQUENCE: 8

```
gcggagcgcg cgcggggttg gttgccgcga gcgtggggga gcgtggaccg cggcgctgct        60
cagcggtggg gctgccttcc cccggccctc ctccctggtc cctggcgagg gcactggcgg       120
cggcggggcc ggggtccgca aggccggaga aggccgccgg gcccgggcat ggtggtctgg       180
ggcaacgcgg aagaagctcc accatgaggc gaggtggatg gaggaagcga gctgaaaatg       240
atggctggga acatggggt gggtatatgg ctgccaaggt ccagaaattg gaggaacagt        300
ttcgatcaga tgctgctatg cagaaggatg ggacttcatc tacaattttt agtggagttg       360
ccatctatgt taatggatac acagatcctt ccgctgagga attgagaaaa ctaatgatgt       420
tgcatggagg tcaataccat gtatattatt ccagatctaa acaacacat attattgcca        480
caaatcttcc caatgccaaa attaaagaat taaggggga aaaagtaatt cgaccagaat        540
ggattgtgga agcatcaaa gctggacgac tcctctccta cattccatat cagctgtaca       600
ccaagcagtc cagtgtgcag aaaggtctca gctttaatcc tgtatgcaga cctgaggatc       660
ctctgccagg tccaagcaat atagccaaac agctcaacaa cagggtaaat cacatcgtta       720
agaagattga acggaaaat gaagtcaaag tcaatggcat gaacagttgg aatgaagaag       780
atgaaaataa tgattttagt tttgtggatc tggagcagac ctctccggga aggaaacaga      840
atggaattcc gcatcccaga gggagcactg ccatttttaa tggacacact cctagctcta       900
atggtgcctt aaagacacag gattgcttgg tgcccatggt caacagtgtt gccagcaggc       960
tttctccagc cttttcccag gaggaggata aggctgagaa gagcagcact gatttcagag      1020
actgcactct gcagcagttg cagcaaagca ccagaaacac agatgctttg cggaatccac      1080
acagaactaa ttctttctca ttatcacctt tgcacagtaa cactaaaatc aatggtgctc      1140
accactccac tgttcagggg ccttcaagca caaaaagcac ttcttcagta tctacgttta      1200
gcaaggcagc accttcagtg ccatccaaac cttcagactg caattttatt tcaaacttct      1260
attctcattc aagactgcat cacatatcaa tgtggaagtg tgaattgact gagttttgtca    1320
ataccctaca aagacaaagt aatggtatct ttccaggaag ggaaaagtta aaaaaaatga      1380
aaacaggcag gtctgcactt gttgtaactg acacaggaga tatgtcagta ttgaattctc      1440
ccagacatca gagctgtata atgcatgttg atatggattg cttctttgta tcagtgggta      1500
tacgaaatag accagatctc aaaggaaaac cagtggctgt acaagtaac agaggcacag       1560
gaagggcacc tttacgtcct ggcgctaacc cccagctgga gtggcagtat taccagaata      1620
aaatcctgaa aggcaaagca gcagatatac cagattcatc attgtgggag aatccagatt      1680
```

-continued

```
ctgcgcaagc aaatggaatt gattctgttt tgtcaagggc tgaaattgca tcttgtagtt   1740
atgaggccag gcaacttggc attaagaacg gaatgttttt tgggcatgct aaacaactat   1800
gtcctaatct tcaagctgtt ccatacgatt ttcatgcata taaggaagtc gcacaaacat   1860
tgtatgaaac attggcaagc tacactcata acattgaagc tgtcagttgt gatgaagcgc   1920
tggtagacat taccgaaatc cttgcagaga ccaaacttac tcctgatgaa tttgcaaatg   1980
ctgttcgtat ggaaatcaaa gaccagacga atgtgctgc ctctgttgga attggttcta   2040
atattctcct ggctagaatg gcaactagaa aagcaaaacc agatgggcag taccacctaa   2100
aaccagaaga agtagatgat tttatcagag gccagctagt gaccaatcta ccaggagttg   2160
gacattcaat ggaatctaag ttggcatctt tgggaattaa acttgtgga gacttgcagt   2220
atatgaccat ggcaaaactc caaaagaat ttggtcccaa acaggtcag atgctttata    2280
ggttctgccg tggcttggat gatagaccag ttcgaactga aaggaaaga aatctgttt    2340
cagctgagat caactatgga ataaggttta ctcagccaaa agaggcagaa gcttttcttc   2400
tgagtctttc agaagaaatt caagaagac tagaagccac tggcatgaag ggtaaacgtc    2460
taactctcaa aatcatggta cgaaagcctg gggctcctgt agaaactgca aaatttggag   2520
gccatggaat ttgtgataac attgccagga ctgtaactct tgaccaggca acagataatg   2580
caaaaataat tggaaaggcg atgctaaaca tgtttcatac aatgaaacta aatatatcag   2640
atatgagagg ggttgggatt cacgtgaatc agttggttcc aactaatctg aacccttcca   2700
catgtcccag tcgcccatca gttcagtcaa gccacttcc tagtgggtca tactctgtcc    2760
gtgatgtctt ccaagttcag aaagctaaga atccaccga agaggagcac aaagaagtat    2820
ttcgggctgc tgtggatctg gaaatatcat ctgcttctag aacttgcact tcttgccac   2880
cttttcctgc acatctgccg accagtcctg tactaacaa ggctgagtct tcagggaaat    2940
ggaatggtct acatactcct gtcagtgtgc agtcgagact taacctgagt atagaggtcc    3000
cgtcaccttc ccagctggat cagtctgttt tagaagcact tccacctgat ctccgggaac    3060
aagtagagca agtctgtgct gtccagcaag cagagtcaca tggcgacaaa aagaaagaac    3120
cagtaaatgg ctgtaataca ggaattttgc cacaaccagt tgggacagtc ttgttgcaaa    3180
taccagaacc tcaagaatcg aacagtgacg caggaataaa tttaatagcc cttccagcat    3240
tttcacaggt ggaccctgag gtatttgctc cccttcctgc tgaacttcag agggagctga    3300
aagcagcgta tgatcaaaga caaaggcagg gcgagaacag cactcaccag cagtcagcca    3360
gcgcatctgt gccaaagaat cctttacttc atctaaaggc agcagtgaaa gaaaagaaaa    3420
gaaacaagaa gaaaaaaacc atcggttcac caaaaaggat tcagagtcct ttgaataaca    3480
agctgcttaa cagtcctgca aaaactctgc caggggcctg tggcagtccc cagaagttaa    3540
ttgatgggtt tctaaaacat gaaggacctc ctgcagagaa acccctggaa gaactctctg    3600
cttctacttc aggtgtgcca ggcctttcta gtttgcagtc tgacccagct ggctgtgtga    3660
gacctccagc acccaatcta gctggagctg ttgaattcaa tgatgtgaag accttgctca    3720
gagaatggat aactacaatt tcagatccaa tggaagaaga cattctccaa gttgtgaaat    3780
actgtactga tctaatagaa gaaaaagatt tggaaaact ggatctagtt ataaaataca     3840
tgaaaaggct gatgcagcaa tcggtggaat cggtttggaa tatggcattt gactttattc    3900
ttgacaatgt ccaggtggtt ttacaacaaa cttatgaag cacattaaaa gttacataaa     3960
tattaccaga gagcctgatg ctctctgata gctgtgccat aagtgcttgt gaggtatttg    4020
```

-continued

```
caaagtgcat gatagtaatg ctcggagttt ttataatttt aaatttcttt taaagcaagt    4080
gttttgtaca tttcttttca aaaagtgcca aatttgtcag tattgcatgt aaataattgt    4140
gttaattatt ttactgtagc atagattcta tttacaaaat gtttgtttat aaagttttat    4200 ggattttac agtgaagtgt ttacagttgt ttaataaaga actgtatgta tattt          4255
```

<210> SEQ ID NO 9
<211> LENGTH: 1251
<212> TYPE: PRT
<213> ORGANISM: Homo sapiens

<400> SEQUENCE: 9

```
Met Arg Arg Gly Gly Trp Arg Lys Arg Ala Glu Asn Asp Gly Trp Glu
1               5                   10                  15

Thr Trp Gly Gly Tyr Met Ala Ala Lys Val Gln Lys Leu Glu Glu Gln
            20                  25                  30

Phe Arg Ser Asp Ala Ala Met Gln Lys Asp Gly Thr Ser Ser Thr Ile
        35                  40                  45

Phe Ser Gly Val Ala Ile Tyr Val Asn Gly Tyr Thr Asp Pro Ser Ala
    50                  55                  60

Glu Glu Leu Arg Lys Leu Met Met Leu His Gly Gly Gln Tyr His Val
65                  70                  75                  80

Tyr Tyr Ser Arg Ser Lys Thr Thr His Ile Ile Ala Thr Asn Leu Pro
                85                  90                  95

Asn Ala Lys Ile Lys Glu Leu Lys Gly Glu Lys Val Ile Arg Pro Glu
            100                 105                 110

Trp Ile Val Glu Ser Ile Lys Ala Gly Arg Leu Leu Ser Tyr Ile Pro
        115                 120                 125

Tyr Gln Leu Tyr Thr Lys Gln Ser Ser Val Gln Lys Gly Leu Ser Phe
    130                 135                 140

Asn Pro Val Cys Arg Pro Glu Asp Pro Leu Pro Gly Pro Ser Asn Ile
145                 150                 155                 160

Ala Lys Gln Leu Asn Asn Arg Val Asn His Ile Val Lys Lys Ile Glu
                165                 170                 175

Thr Glu Asn Glu Val Lys Val Asn Gly Met Asn Ser Trp Asn Glu Glu
            180                 185                 190

Asp Glu Asn Asn Asp Phe Ser Phe Val Asp Leu Glu Gln Thr Ser Pro
        195                 200                 205

Gly Arg Lys Gln Asn Gly Ile Pro His Pro Arg Gly Ser Thr Ala Ile
    210                 215                 220

Phe Asn Gly His Thr Pro Ser Asn Gly Ala Leu Lys Thr Gln Asp
225                 230                 235                 240

Cys Leu Val Pro Met Val Asn Ser Val Ala Ser Arg Leu Ser Pro Ala
                245                 250                 255

Phe Ser Gln Glu Glu Asp Lys Ala Glu Lys Ser Ser Thr Asp Phe Arg
            260                 265                 270

Asp Cys Thr Leu Gln Gln Leu Gln Gln Ser Thr Arg Asn Thr Asp Ala
        275                 280                 285

Leu Arg Asn Pro His Arg Thr Asn Ser Phe Ser Leu Ser Pro Leu His
    290                 295                 300

Ser Asn Thr Lys Ile Asn Gly Ala His His Ser Thr Val Gln Gly Pro
305                 310                 315                 320

Ser Ser Thr Lys Ser Thr Ser Ser Val Ser Thr Phe Ser Lys Ala Ala
                325                 330                 335
```

```
Pro Ser Val Pro Ser Lys Pro Ser Asp Cys Asn Phe Ile Ser Asn Phe
        340                 345                 350

Tyr Ser His Ser Arg Leu His His Ile Ser Met Trp Lys Cys Glu Leu
        355                 360                 365

Thr Glu Phe Val Asn Thr Leu Gln Arg Gln Ser Asn Gly Ile Phe Pro
        370                 375                 380

Gly Arg Glu Lys Leu Lys Lys Met Lys Thr Gly Arg Ser Ala Leu Val
385                 390                 395                 400

Val Thr Asp Thr Gly Asp Met Ser Val Leu Asn Ser Pro Arg His Gln
                405                 410                 415

Ser Cys Ile Met His Val Asp Met Asp Cys Phe Phe Val Ser Val Gly
                420                 425                 430

Ile Arg Asn Arg Pro Asp Leu Lys Gly Lys Pro Val Ala Val Thr Ser
                435                 440                 445

Asn Arg Gly Thr Gly Arg Ala Pro Leu Arg Pro Gly Ala Asn Pro Gln
                450                 455                 460

Leu Glu Trp Gln Tyr Tyr Gln Asn Lys Ile Leu Lys Gly Lys Ala Ala
465                 470                 475                 480

Asp Ile Pro Asp Ser Ser Leu Trp Glu Asn Pro Asp Ser Ala Gln Ala
                485                 490                 495

Asn Gly Ile Asp Ser Val Leu Ser Arg Ala Glu Ile Ala Ser Cys Ser
                500                 505                 510

Tyr Glu Ala Arg Gln Leu Gly Ile Lys Asn Gly Met Phe Phe Gly His
                515                 520                 525

Ala Lys Gln Leu Cys Pro Asn Leu Gln Ala Val Pro Tyr Asp Phe His
        530                 535                 540

Ala Tyr Lys Glu Val Ala Gln Thr Leu Tyr Glu Thr Leu Ala Ser Tyr
545                 550                 555                 560

Thr His Asn Ile Glu Ala Val Ser Cys Asp Glu Ala Leu Val Asp Ile
                565                 570                 575

Thr Glu Ile Leu Ala Glu Thr Lys Leu Thr Pro Asp Glu Phe Ala Asn
                580                 585                 590

Ala Val Arg Met Glu Ile Lys Asp Gln Thr Lys Cys Ala Ala Ser Val
        595                 600                 605

Gly Ile Gly Ser Asn Ile Leu Leu Ala Arg Met Ala Thr Arg Lys Ala
        610                 615                 620

Lys Pro Asp Gly Gln Tyr His Leu Lys Pro Glu Glu Val Asp Asp Phe
625                 630                 635                 640

Ile Arg Gly Gln Leu Val Thr Asn Leu Pro Gly Val Gly His Ser Met
                645                 650                 655

Glu Ser Lys Leu Ala Ser Leu Gly Ile Lys Thr Cys Gly Asp Leu Gln
                660                 665                 670

Tyr Met Thr Met Ala Lys Leu Gln Lys Glu Phe Gly Pro Lys Thr Gly
        675                 680                 685

Gln Met Leu Tyr Arg Phe Cys Arg Gly Leu Asp Asp Arg Pro Val Arg
        690                 695                 700

Thr Glu Lys Glu Arg Lys Ser Val Ser Ala Glu Ile Asn Tyr Gly Ile
705                 710                 715                 720

Arg Phe Thr Gln Pro Lys Glu Ala Glu Phe Leu Leu Ser Leu Ser
                725                 730                 735

Glu Glu Ile Gln Arg Arg Leu Glu Ala Thr Gly Met Lys Gly Lys Arg
                740                 745                 750

Leu Thr Leu Lys Ile Met Val Arg Lys Pro Gly Ala Pro Val Glu Thr
```

```
                755                 760                 765
Ala Lys Phe Gly Gly His Gly Ile Cys Asp Asn Ile Ala Arg Thr Val
770                 775                 780

Thr Leu Asp Gln Ala Thr Asp Asn Ala Lys Ile Ile Gly Lys Ala Met
785                 790                 795                 800

Leu Asn Met Phe His Thr Met Lys Leu Asn Ile Ser Asp Met Arg Gly
                    805                 810                 815

Val Gly Ile His Val Asn Gln Leu Val Pro Thr Asn Leu Asn Pro Ser
                820                 825                 830

Thr Cys Pro Ser Arg Pro Ser Val Gln Ser Ser His Phe Pro Ser Gly
                835                 840                 845

Ser Tyr Ser Val Arg Asp Val Phe Gln Val Gln Lys Ala Lys Lys Ser
850                 855                 860

Thr Glu Glu His Lys Glu Val Phe Arg Ala Ala Val Asp Leu Glu
865                 870                 875                 880

Ile Ser Ser Ala Ser Arg Thr Cys Thr Phe Leu Pro Pro Phe Pro Ala
                885                 890                 895

His Leu Pro Thr Ser Pro Asp Thr Asn Lys Ala Glu Ser Ser Gly Lys
                900                 905                 910

Trp Asn Gly Leu His Thr Pro Val Ser Val Gln Ser Arg Leu Asn Leu
                915                 920                 925

Ser Ile Glu Val Pro Ser Pro Ser Gln Leu Asp Gln Ser Val Leu Glu
930                 935                 940

Ala Leu Pro Pro Asp Leu Arg Glu Gln Val Glu Gln Val Cys Ala Val
945                 950                 955                 960

Gln Gln Ala Glu Ser His Gly Asp Lys Lys Glu Pro Val Asn Gly
                965                 970                 975

Cys Asn Thr Gly Ile Leu Pro Gln Pro Val Gly Thr Val Leu Leu Gln
                980                 985                 990

Ile Pro Glu Pro Gln Glu Ser Asn Ser Asp Ala Gly Ile Asn Leu Ile
                995                 1000                1005

Ala Leu Pro Ala Phe Ser Gln Val Asp Pro Glu Val Phe Ala Ala
        1010                1015                1020

Leu Pro Ala Glu Leu Gln Arg Glu Leu Lys Ala Ala Tyr Asp Gln
        1025                1030                1035

Arg Gln Arg Gln Gly Glu Asn Ser Thr His Gln Gln Ser Ala Ser
        1040                1045                1050

Ala Ser Val Pro Lys Asn Pro Leu Leu His Leu Lys Ala Ala Val
        1055                1060                1065

Lys Glu Lys Lys Arg Asn Lys Lys Lys Thr Ile Gly Ser Pro
        1070                1075                1080

Lys Arg Ile Gln Ser Pro Leu Asn Asn Lys Leu Leu Asn Ser Pro
        1085                1090                1095

Ala Lys Thr Leu Pro Gly Ala Cys Gly Ser Pro Gln Lys Leu Ile
        1100                1105                1110

Asp Gly Phe Leu Lys His Glu Gly Pro Pro Ala Glu Lys Pro Leu
        1115                1120                1125

Glu Glu Leu Ser Ala Ser Thr Ser Gly Val Pro Gly Leu Ser Ser
        1130                1135                1140

Leu Gln Ser Asp Pro Ala Gly Cys Val Arg Pro Ala Pro Asn
        1145                1150                1155

Leu Ala Gly Ala Val Glu Phe Asn Asp Val Lys Thr Leu Leu Arg
        1160                1165                1170
```

-continued

```
Glu Trp Ile Thr Thr Ile Ser Asp Pro Met Glu Glu Asp Ile Leu
    1175                1180                1185

Gln Val Val Lys Tyr Cys Thr Asp Leu Ile Glu Glu Lys Asp Leu
    1190                1195                1200

Glu Lys Leu Asp Leu Val Ile Lys Tyr Met Lys Arg Leu Met Gln
    1205                1210                1215

Gln Ser Val Glu Ser Val Trp Asn Met Ala Phe Asp Phe Ile Leu
    1220                1225                1230

Asp Asn Val Gln Val Val Leu Gln Gln Thr Tyr Gly Ser Thr Leu
    1235                1240                1245

Lys Val Thr
    1250

<210> SEQ ID NO 10
<211> LENGTH: 85
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (17)..(22)
<223> OTHER INFORMATION: Gap in alignment
<220> FEATURE:
<221> NAME/KEY: MISC_FEATURE
<222> LOCATION: (50)..(60)
<223> OTHER INFORMATION: Gap in alignment
<220> FEATURE:
<221> NAME/KEY: MISC_FEATURE
<222> LOCATION: (30)..(33)
<223> OTHER INFORMATION: Gap in alignment

<400> SEQUENCE: 10

Ile Met Glu Gly Phe Ser Val Phe Val Asn Gly Tyr Thr Asp Pro Pro
1               5                   10                  15

Xaa Xaa Xaa Xaa Xaa Xaa Leu Met Ile Ser His Gly Gly Xaa Xaa Xaa
                20                  25                  30

Xaa Tyr Tyr Gln His Gly Ile Thr Ser Tyr Thr Ile Ala Ser Ser Ile
            35                  40                  45

Ala Xaa Xaa Xaa Xaa Xaa Xaa Xaa Xaa Xaa Xaa Xaa Ile Phe Ile Lys
    50                  55                  60

Ala Asp Trp Ile Thr Glu Ser Ile Ala Ala Gly Lys Pro Leu Asp Tyr
65                  70                  75                  80

Arg Asp Phe Leu Ile
                85

<210> SEQ ID NO 11
<211> LENGTH: 32
<212> TYPE: PRT
<213> ORGANISM: C. elegans, A. thaliana, S. cerevisiae, S. pombe and H.
      sapiens

<400> SEQUENCE: 11

Arg Asn Pro Asn Phe Ile Arg Asp Tyr Tyr Ala Arg Ser Arg Leu His
1               5                   10                  15

Leu Ile Ser Thr Leu Ala Gln Asp Met Lys Asp Phe Val Ala Asn Leu
                20                  25                  30

<210> SEQ ID NO 12
<211> LENGTH: 39
<212> TYPE: PRT
<213> ORGANISM: C. elegans, A. thaliana, S. cerevisiae, S. pombe and H.
      sapiens
```

```
<220> FEATURE:
<221> NAME/KEY: MISC_FEATURE
<222> LOCATION: (6)..(8)
<223> OTHER INFORMATION: Gap in alignment
<220> FEATURE:
<221> NAME/KEY: MISC_FEATURE
<222> LOCATION: (23)..(28)
<223> OTHER INFORMATION: Gap in alignment

<400> SEQUENCE: 12

Val Phe His Val Asp Xaa Xaa Xaa Leu Asp Cys Phe Phe Val Ser Val
1               5                   10                  15

Ala Val Arg Asn Arg Ile Xaa Xaa Xaa Xaa Xaa Asp Leu Lys His
            20                  25                  30

Lys Glu Val Ala Ile Thr His
        35

<210> SEQ ID NO 13
<211> LENGTH: 49
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (33)..(35)
<223> OTHER INFORMATION: Gap in alignment

<400> SEQUENCE: 13

Ser Met Ser Glu Val Ala Ser Cys Ser Tyr Ala Ala Arg Asp Cys Gly
1               5                   10                  15

Val Lys Asn Gly Met Leu Val Arg Asp Ala Leu Gln Lys Cys Pro Gln
            20                  25                  30

Xaa Xaa Xaa Leu Thr Leu Leu Pro Tyr Gln Phe Glu Asp Tyr Val Gln
        35                  40                  45

Val

<210> SEQ ID NO 14
<211> LENGTH: 9
<212> TYPE: PRT
<213> ORGANISM: C. elegans, A. thaliana, S. cerevisiae, S. pombe and H.
      sapiens

<400> SEQUENCE: 14

Val Ser Cys Asp Glu Met Tyr Ile Asn
1               5

<210> SEQ ID NO 15
<211> LENGTH: 75
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (15)..(15)
<223> OTHER INFORMATION: Gap in alignment
<220> FEATURE:
<221> NAME/KEY: MISC_FEATURE
<222> LOCATION: (42)..(42)
<223> OTHER INFORMATION: Gap in alignment

<400> SEQUENCE: 15

Leu Ala Glu His Ile Arg Lys Val Ile Arg Glu Lys Thr Gln Xaa Cys
1               5                   10                  15

Pro Ala Ser Val Gly Ile Gly Ser Thr Ser Leu Leu Ala Arg Leu Ala
            20                  25                  30
```

```
Thr Arg His Ala Lys Pro Asp Gly Val Xaa Phe Trp Val Asn Ala His
        35                  40                  45

Lys Lys Asn Glu Phe Ile Ser Glu Glu Lys Val Lys Asp Leu Pro Gly
 50                  55                  60

Phe Gly Tyr Glu Met Met Asn Arg Leu Thr Ser
 65                  70                  75
```

<210> SEQ ID NO 16
<211> LENGTH: 87
<212> TYPE: PRT
<213> ORGANISM: C. elegans, A. thaliana, S. cerevisiae, S. pombe and H. sapiens
<220> FEATURE:
<221> NAME/KEY: MISC_FEATURE
<222> LOCATION: (17)..(22)
<223> OTHER INFORMATION: Gap in alignment
<220> FEATURE:
<221> NAME/KEY: MISC_FEATURE
<222> LOCATION: (52)..(62)
<223> OTHER INFORMATION: Gap in alignment
<220> FEATURE:
<221> NAME/KEY: MISC_FEATURE
<222> LOCATION: (30)..(35)
<223> OTHER INFORMATION: Gap in alignment

<400> SEQUENCE: 16

```
Ile Phe Gln Gly Val Ser Ile Phe Val Asp Gly Phe Thr Ile Pro Ser
 1               5                  10                  15

Xaa Xaa Xaa Xaa Xaa Xaa Arg Ile Thr Cys Cys Glu Thr Xaa Xaa Xaa
                20                  25                  30

Xaa Xaa Xaa Tyr Leu Cys Gln Gln Thr Ser Gly Leu Ser His Leu Thr
        35                  40                  45

Pro Gln Met Xaa Xaa Xaa Xaa Xaa Xaa Xaa Xaa Xaa Xaa Xaa Gly Tyr
 50                  55                  60

Ser Glu Ala Glu Glu Gly Ser Ser Ile Arg Ala Asp Asp Ser Glu Glu
 65                  70                  75                  80

Ala Arg Asp His Ile Asp Asp
                85
```

<210> SEQ ID NO 17
<211> LENGTH: 32
<212> TYPE: PRT
<213> ORGANISM: C. elegans, A. thaliana, S. cerevisiae, S. pombe and H. sapiens
<220> FEATURE:
<221> NAME/KEY: MISC_FEATURE
<222> LOCATION: (23)..(25)
<223> OTHER INFORMATION: Gap in alignment

<400> SEQUENCE: 17

```
Glu Asp Pro Asn Phe Val Glu Asn Tyr Phe Lys Asn Ser Arg Leu His
 1               5                  10                  15

Phe Ile Gly Thr Trp Arg Xaa Xaa Xaa Asn Arg Tyr Arg Lys Arg Phe
                20                  25                  30
```

<210> SEQ ID NO 18
<211> LENGTH: 39
<212> TYPE: PRT
<213> ORGANISM: C. elegans, A. thaliana, S. cerevisiae, S. pombe and H. sapiens
<220> FEATURE:
<221> NAME/KEY: MISC_FEATURE
<222> LOCATION: (23)..(28)
<223> OTHER INFORMATION: Gap in alignment

<400> SEQUENCE: 18

```
Leu Phe Glu Ser Val Lys Tyr Phe Gln Asp Cys Phe Val Ser Val
1               5                  10                 15

Val Ile Lys Asn Arg Leu Xaa Xaa Xaa Xaa Xaa Glu Leu His Asp
            20                 25                 30

Lys Pro Val Ala Val Cys His
            35
```

<210> SEQ ID NO 19
<211> LENGTH: 49
<212> TYPE: PRT
<213> ORGANISM: C. elegans, A. thaliana, S. cerevisiae, S. pombe and H. sapiens
<220> FEATURE:
<221> NAME/KEY: MISC_FEATURE
<222> LOCATION: (33)..(35)
<223> OTHER INFORMATION: Gap in alignment

<400> SEQUENCE: 19

```
Gly Thr Ala Glu Ile Ser Ser Ala Asn Tyr Pro Ala Arg Ala Tyr Gly
1               5                  10                 15

Val Lys Ala Gly Met Phe Val Arg His Ala Lys Asp Leu Cys Pro Gln
            20                 25                 30

Xaa Xaa Xaa Leu Val Ile Val Pro Tyr Asn Phe Glu Ala Tyr Glu Glu
            35                 40                 45

Ala
```

<210> SEQ ID NO 20
<211> LENGTH: 9
<212> TYPE: PRT
<213> ORGANISM: C. elegans, A. thaliana, S. cerevisiae, S. pombe and H. sapiens

<400> SEQUENCE: 20

```
Leu Ser Cys Asp Glu Ala Phe Leu Asp
1               5
```

<210> SEQ ID NO 21
<211> LENGTH: 75
<212> TYPE: PRT
<213> ORGANISM: C. elegans, A. thaliana, S. cerevisiae, S. pombe and H. sapiens
<220> FEATURE:
<221> NAME/KEY: MISC_FEATURE
<222> LOCATION: (15)..(15)
<223> OTHER INFORMATION: Gap in alignment
<220> FEATURE:
<221> NAME/KEY: MISC_FEATURE
<222> LOCATION: (42)..(42)
<223> OTHER INFORMATION: Gap in alignment

<400> SEQUENCE: 21

```
Leu Ala Ser Thr Ile Arg Asn Glu Ile Leu Glu Thr Thr Gly Xaa Cys
1               5                  10                 15

Ser Ala Ser Ala Gly Ile Gly Gly Thr Met Leu Met Ala Arg Leu Ala
            20                 25                 30

Thr Arg Val Ala Lys Pro Ala Gly Gln Xaa Leu Tyr Ile Ser Ala Glu
            35                 40                 45

Lys Val Glu Glu Phe Leu Asp Gln Leu Pro Val Gly Thr Leu Pro Gly
        50                 55                 60

Val Gly Ser Val Leu Lys Glu Lys Leu Val Lys
65                  70                 75
```

```
<210> SEQ ID NO 22
<211> LENGTH: 85
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (17)..(23)
<223> OTHER INFORMATION: Gap in alignment
<220> FEATURE:
<221> NAME/KEY: MISC_FEATURE
<222> LOCATION: (30)..(33)
<223> OTHER INFORMATION: Gap in alignment
<220> FEATURE:
<221> NAME/KEY: MISC_FEATURE
<222> LOCATION: (50)..(60)
<223> OTHER INFORMATION: Gap in alignment

<400> SEQUENCE: 22

Ile Phe Lys Asn Cys Val Ile Tyr Ile Asn Gly Tyr Thr Lys Pro Gly
1               5                   10                  15

Xaa Xaa Xaa Xaa Xaa Xaa Met Ile Val Leu His Gly Gly Xaa Xaa Xaa
            20                  25                  30

Xaa Tyr Leu Ser Ser Lys Lys Thr Val Thr His Ile Val Ala Ser Asn
        35                  40                  45

Leu Xaa Xaa Xaa Xaa Xaa Xaa Xaa Xaa Xaa Xaa Lys Val Val Ser
    50                  55                  60

Pro Asp Trp Ile Val Asp Ser Val Lys Glu Ala Arg Leu Leu Pro Trp
65                  70                  75                  80

Gln Asn Tyr Ser Leu
            85

<210> SEQ ID NO 23
<211> LENGTH: 32
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (23)..(25)
<223> OTHER INFORMATION: Gap in alignment

<400> SEQUENCE: 23

Asp Asp Pro Asp Phe Leu Thr Ser Tyr Phe Ala His Ser Arg Leu His
1               5                   10                  15

His Leu Ser Ala Trp Lys Xaa Xaa Xaa Ala Asn Leu Lys Asp Lys Phe
            20                  25                  30

<210> SEQ ID NO 24
<211> LENGTH: 39
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (6)..(8)
<223> OTHER INFORMATION: Gap in alignment

<400> SEQUENCE: 24

Ile Phe His Ile Asp Xaa Xaa Xaa Phe Asp Cys Phe Phe Ala Thr Val
1               5                   10                  15

Ala Tyr Leu Cys Arg Ser Ser Ser Phe Ser Ala Cys Asp Phe Lys Arg
            20                  25                  30

Asp Pro Ile Val Val Cys His
            35
```

-continued

<210> SEQ ID NO 25
<211> LENGTH: 49
<212> TYPE: PRT
<213> ORGANISM: C. elegans, A. thaliana, S. cerevisiae, S. pombe and H. sapiens

<400> SEQUENCE: 25

Lys Asn Ser Asp Ile Ala Ser Cys Asn Tyr Val Ala Arg Ser Tyr Gly
1               5                   10                  15

Ile Lys Asn Gly Met Trp Val Ser Gln Ala Glu Lys Met Leu Pro Asn
            20                  25                  30

Gly Ile Lys Leu Ile Ser Leu Pro Tyr Thr Phe Glu Gln Phe Gln Leu
        35                  40                  45

Lys

<210> SEQ ID NO 26
<211> LENGTH: 9
<212> TYPE: PRT
<213> ORGANISM: C. elegans, A. thaliana, S. cerevisiae, S. pombe and H. sapiens

<400> SEQUENCE: 26

Ile Ser Ile Asp Glu Ala Val Cys Val
1               5

<210> SEQ ID NO 27
<211> LENGTH: 75
<212> TYPE: PRT
<213> ORGANISM: C. elegans, A. thaliana, S. cerevisiae, S. pombe and H. sapiens

<400> SEQUENCE: 27

Leu Cys Glu Glu Ile Arg Gln Glu Ile Phe Gln Gly Thr Asn Gly Cys
1               5                   10                  15

Thr Val Ser Ile Gly Cys Ser Asp Ser Leu Val Leu Ala Arg Leu Ala
            20                  25                  30

Leu Lys Met Ala Lys Pro Asn Gly Tyr Asn Ile Thr Phe Lys Ser Asn
        35                  40                  45

Leu Ser Glu Glu Phe Trp Ser Ser Phe Lys Leu Asp Asp Leu Pro Gly
    50                  55                  60

Val Gly His Ser Thr Leu Ser Arg Leu Glu Ser
65                  70                  75

<210> SEQ ID NO 28
<211> LENGTH: 85
<212> TYPE: PRT
<213> ORGANISM: C. elegans, A. thaliana, S. cerevisiae, S. pombe and H. sapiens
<220> FEATURE:
<221> NAME/KEY: MISC_FEATURE
<222> LOCATION: (17)..(22)
<223> OTHER INFORMATION: Gap in alignment
<220> FEATURE:
<221> NAME/KEY: MISC_FEATURE
<222> LOCATION: (30)..(33)
<223> OTHER INFORMATION: Gap in alignment
<220> FEATURE:
<221> NAME/KEY: MISC_FEATURE
<222> LOCATION: (50)..(60)
<223> OTHER INFORMATION: Gap in alignment

<400> SEQUENCE: 28

Leu Phe His Gly Leu Ala Ile Ala Ile Asn Gly Tyr Thr Lys Pro Ser

```
                1               5                   10                  15
Xaa Xaa Xaa Xaa Xaa Xaa Met Ile Val Ser Asn Gly Gly Xaa Xaa Xaa
                    20                  25                  30

Xaa Tyr Val Asp Gly Lys Thr Ser Ile Ser Tyr Leu Val Cys Ser Phe
            35                  40                  45

Leu Xaa Xaa Xaa Xaa Xaa Xaa Xaa Xaa Xaa Xaa Lys Val Val Lys
        50                  55                  60

Pro Glu Trp Ile Val Asp Cys Ile Lys Gln Lys Lys Ile Leu Pro Trp
65              70                  75                  80

Ile Asn Tyr Arg Thr
                85
```

<210> SEQ ID NO 29
<211> LENGTH: 32
<212> TYPE: PRT
<213> ORGANISM: C. elegans, A. thaliana, S. cerevisiae, S. pombe and H. sapiens
<220> FEATURE:
<221> NAME/KEY: MISC_FEATURE
<222> LOCATION: (23)..(25)
<223> OTHER INFORMATION: Gap in alignment

<400> SEQUENCE: 29

```
Gln Asn Gln Asp Phe Leu Glu Asn Phe Phe Ser Ser Ser Arg Leu His
1               5                   10                  15

His Leu Ser Thr Trp Lys Xaa Xaa Xaa Ala Asp Phe Lys Asn Glu Ile
            20                  25                  30
```

<210> SEQ ID NO 30
<211> LENGTH: 39
<212> TYPE: PRT
<213> ORGANISM: C. elegans, A. thaliana, S. cerevisiae, S. pombe and H. sapiens
<220> FEATURE:
<221> NAME/KEY: MISC_FEATURE
<222> LOCATION: (6)..(8)
<223> OTHER INFORMATION: Gap in alignment
<220> FEATURE:
<221> NAME/KEY: MISC_FEATURE
<222> LOCATION: (23)..(28)
<223> OTHER INFORMATION: Gap in alignment

<400> SEQUENCE: 30

```
Leu Leu His Val Asp Xaa Xaa Xaa Phe Asp Cys Phe Phe Ala Ser Val
1               5                   10                  15

Ser Thr Arg Phe Ser His Xaa Xaa Xaa Xaa Xaa Xaa Glu Leu Arg Leu
            20                  25                  30

Lys Pro Val Ala Val Ala His
                35
```

<210> SEQ ID NO 31
<211> LENGTH: 49
<212> TYPE: PRT
<213> ORGANISM: C. elegans, A. thaliana, S. cerevisiae, S. pombe and H. sapiens
<220> FEATURE:
<221> NAME/KEY: MISC_FEATURE
<222> LOCATION: (33)..(35)
<223> OTHER INFORMATION: Gap in alignment

<400> SEQUENCE: 31

```
Lys Asn Ser Glu Ile Ala Ser Cys Asn Tyr Glu Ala Arg Lys Phe Gly
1               5                   10                  15

Ile Lys Asn Gly Met Tyr Val Gly Thr Ala Lys Asn Leu Cys Pro Ser
```

-continued

```
                20                  25                  30
Xaa Xaa Xaa Leu Arg Val Val Asp Tyr Asp Phe Gly Ala Tyr Glu Ser
        35                  40                  45
Val

<210> SEQ ID NO 32
<211> LENGTH: 9
<212> TYPE: PRT
<213> ORGANISM: C. elegans, A. thaliana, S. cerevisiae, S. pombe and H.
      sapiens

<400> SEQUENCE: 32

Ile Ser Ile Asp Glu Ala Leu Leu Asp
1               5

<210> SEQ ID NO 33
<211> LENGTH: 75
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (15)..(15)
<223> OTHER INFORMATION: Gap in alignment
<220> FEATURE:
<221> NAME/KEY: MISC_FEATURE
<222> LOCATION: (42)..(42)
<223> OTHER INFORMATION: Gap in alignment

<400> SEQUENCE: 33

Ile Ala Glu Ser Ile Arg Ser Gln Val Arg Glu Lys Thr Asn Xaa Cys
1               5                   10                  15

Glu Val Ser Val Gly Ile Gly Pro Asn Val Leu Leu Ala Arg Leu Ala
            20                  25                  30

Leu Arg Lys Ala Lys Pro His Asn Val Xaa Tyr Ser Leu Ser Ile Glu
        35                  40                  45

Asn Val Phe Asp Val Leu Ser Pro Leu Ser Val Gln Asp Leu Pro Gly
    50                  55                  60

Val Gly Ser Ser Gln Ala Gln Lys Leu Phe Asn
65                  70                  75

<210> SEQ ID NO 34
<211> LENGTH: 85
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (17)..(22)
<223> OTHER INFORMATION: Gap in alignment
<220> FEATURE:
<221> NAME/KEY: MISC_FEATURE
<222> LOCATION: (30)..(33)
<223> OTHER INFORMATION: Gap in alignment
<220> FEATURE:
<221> NAME/KEY: MISC_FEATURE
<222> LOCATION: (41)..(41)
<223> OTHER INFORMATION: Gap in alignment
<220> FEATURE:
<221> NAME/KEY: MISC_FEATURE
<222> LOCATION: (50)..(60)
<223> OTHER INFORMATION: Gap in alignment

<400> SEQUENCE: 34

Ile Phe Ser Gly Val Ala Ile Tyr Val Asn Gly Tyr Thr Asp Pro Ser
1               5                   10                  15
```

```
Xaa Xaa Xaa Xaa Xaa Xaa Leu Met Met Leu His Gly Gly Xaa Xaa Xaa
                20                  25                  30

Xaa Tyr Tyr Ser Arg Ser Lys Thr Xaa Thr His Ile Ile Ala Thr Asn
        35                  40                  45

Leu Xaa Xaa Xaa Xaa Xaa Xaa Xaa Xaa Xaa Lys Val Ile Arg
    50                  55                  60

Pro Glu Trp Ile Val Glu Ser Ile Lys Ala Gly Arg Leu Leu Ser Tyr
65                  70                  75                  80

Ile Pro Tyr Gln Leu
                85

<210> SEQ ID NO 35
<211> LENGTH: 32
<212> TYPE: PRT
<213> ORGANISM: C. elegans, A. thaliana, S. cerevisiae, S. pombe and H.
      sapiens

<400> SEQUENCE: 35

Ser Asp Cys Asn Phe Ile Ser Asn Phe Tyr Ser His Ser Arg Leu His
1               5                   10                  15

His Ile Ser Met Trp Lys Cys Glu Leu Thr Glu Phe Val Asn Thr Leu
                20                  25                  30

<210> SEQ ID NO 36
<211> LENGTH: 39
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (6)..(8)
<223> OTHER INFORMATION: Gap in alignment
<220> FEATURE:
<221> NAME/KEY: MISC_FEATURE
<222> LOCATION: (23)..(28)
<223> OTHER INFORMATION: Gap in alignment

<400> SEQUENCE: 36

Ile Met His Val Asp Xaa Xaa Xaa Met Asp Cys Phe Phe Val Ser Val
1               5                   10                  15

Gly Ile Arg Asn Arg Pro Xaa Xaa Xaa Xaa Xaa Xaa Asp Leu Lys Gly
                20                  25                  30

Lys Pro Val Ala Val Thr Ser
            35

<210> SEQ ID NO 37
<211> LENGTH: 49
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (33)..(35)
<223> OTHER INFORMATION: Gap in alignment

<400> SEQUENCE: 37

Ser Arg Ala Glu Ile Ala Ser Cys Ser Tyr Glu Ala Arg Gln Leu Gly
1               5                   10                  15

Ile Lys Asn Gly Met Phe Phe Gly His Ala Lys Gln Leu Cys Pro Asn
                20                  25                  30

Xaa Xaa Xaa Leu Gln Ala Val Pro Tyr Asp Phe His Ala Tyr Lys Glu
            35                  40                  45

Val
```

```
<210> SEQ ID NO 38
<211> LENGTH: 9
<212> TYPE: PRT
<213> ORGANISM: C. elegans, A. thaliana, S. cerevisiae, S. pombe and H.
      sapiens

<400> SEQUENCE: 38

Val Ser Cys Asp Glu Ala Leu Val Asp
1               5

<210> SEQ ID NO 39
<211> LENGTH: 75
<212> TYPE: PRT
<213> ORGANISM: C. elegans, A. thaliana, S. cerevisiae, S. pombe and H.
      sapiens
<220> FEATURE:
<221> NAME/KEY: MISC_FEATURE
<222> LOCATION: (15)..(15)
<223> OTHER INFORMATION: Gap in alignment
<220> FEATURE:
<221> NAME/KEY: MISC_FEATURE
<222> LOCATION: (42)..(42)
<223> OTHER INFORMATION: Gap in alignment

<400> SEQUENCE: 39

Phe Ala Asn Ala Val Arg Met Glu Ile Lys Asp Gln Thr Lys Xaa Cys
1               5                   10                  15

Ala Ala Ser Val Gly Ile Gly Ser Asn Ile Leu Leu Ala Arg Met Ala
            20                  25                  30

Thr Arg Lys Ala Lys Pro Asp Gly Gln Xaa Tyr His Leu Lys Pro Glu
        35                  40                  45

Glu Val Asp Asp Phe Ile Arg Gly Gln Leu Val Thr Asn Leu Pro Gly
    50                  55                  60

Val Gly His Ser Met Glu Ser Lys Leu Ala Ser
65                  70                  75
```

NUCLEIC ACID ENCODING HUMAN REV1 PROTEIN

RELATED APPLICATIONS

This application claims priority from U.S. Provisional Application Serial No. 60/162,140, filed Oct. 29, 1999, incorporated herein by reference.

FIELD OF THE INVENTION

The present invention relates to the cloning and expression of a human gene encoding a protein having deoxycytidyl (dCMP) transferase activity. The present invention also provides methods for expressing the gene, and cancer treating methods using inhibitors to the gene.

BACKGROUND OF THE INVENTION

DNA damage can lead to mutations during replication. In the yeast *S. cerevisiae,* it appears that the majority of induced mutations are generated through the damage-induced mutagenesis pathway (1,2). The required yeast genes in this pathway include: RAD6, RAD18, REV1, REV3, REV6, REV7, and NGM2 (1–7), most of which have been isolated by gene cloning. As expected, inactivating these mutagenesis genes dramatically decreases the mutation frequency following DNA damage (3,8).

Rad6 is a ubiquitin-conjugating enzyme (9) and forms a complex with Rad18 (10–12). It has been proposed that this complex may play an important role in the initial steps of the damage-induced mutagenesis pathway (10). Rev3 protein is a DNA polymerase (DNA polymerase ζ) capable of trans-lesion DNA synthesis (13). In contrast to the replicative DNA polymerases, deletion of the yeast REV3 gene does not lead to lethality (1). Hence, this polymerase is specifically required for damage-induced mutagenesis in yeast. Rev1 belongs to the UmuC family of proteins (14). It possesses a deoxycytidyl (dCMP) transferase activity in a template-dependent reaction, which can efficiently insert a dCMP opposite a template AP (apurinic/apyrimidinic) site (15). Yeast Rad30, an *E. coli* DinB homologue, is another member of the UmuC family (14,16,17). However, unlike Rev1, Rad30 is not a component of the damage-induced mutagenesis pathway, but appears to be involved in a novel error-free lesion bypass mechanism (16,17). Most recently, Rad30 was shown to be a nonessential DNA polymerase (pol η) capable of error-free translesion DNA synthesis opposite a TT dimer in vitro (18). Apparently, the UmuC family of proteins are involved in different mechanisms in the damage tolerance response to unrepaired DNA lesions during replication.

It is only very recently that the damage-induced mutagenesis pathway in humans has been investigated. Two human homologues of the yeast RAD6 gene have been identified: HHR6A and HHR6B (19,20). Additionally, hREV3 has been isolated as the human homologue of the yeast mutagenic DNA polymerase ζ (21,22). Thus, it is most likely that a damage-induced mutagenesis pathway similar to that in yeast is operational in humans. Given the genetic complexity of the yeast mutagenesis pathway, it is certain that more human mutagenesis genes remain to be identified. Since mutations are the building blocks of human cancers, understanding the damage-induced mutagenesis pathway in humans is a key to the understanding of carcinogenesis. Isolating the human mutagenesis genes and elucidating the activities of these gene products are essential steps in these studies.

There is always a need for more effectively diagnosing, preventing and treating cancer. This applies to the determination of polypeptides that are involved in causing mutations that lead to the formation of tumors and further mutations that cause metastasis to occur.

SUMMARY OF THE INVENTION

Applicants have isolated a full-length cDNA representing the homologue of the yeast Rev1 mutagenesis protein. Applicants also determined the chromosomal location of the human REV1 gene and demonstrated its ubiquitous expression in various human tissues. Furthermore, Applicants have demonstrated that the human REV1 protein is a dCMP transferase capable of inserting a dCMP opposite a template AP site.

The present invention also relates to antibodies, including monoclonal or polyclonal antibodies, and antibody fragments that have specific interaction with epitopes present on hREV1. The present invention is also directed to methods of preventing, treating, or ameliorating a disease condition or disorder in an individual comprising the step of administering a therapeutically effective amount of hREV1 protein or its inhibitor or activator to the individual. The present invention is also directed to methods or protocols in treatment or prevention of a disease or disorder based on the gene and gene product described in the present application.

The present invention is related to an isolated nucleic acid molecule that encodes:

- a polynucleotide which encodes the polypeptide set forth in Table 1;
- a polynucleotide which encodes a variant of the polypeptide set forth in Table 1 wherein said variant has a deoxycytidyl transferase activity;
- a polynucleotide which encodes a homologous variant of said polypeptide set forth in Table 1 having less than about 750 amino acid changes; or
- a polynucleotide sequence which hybridizes to the polynucleotide of Table 1 under the following conditions:
  prehybridize the membrane in solution of 0.25M sodium phosphate, 0.25 M NaCl, 1 mM EDTA, 5%SDS and 50% formamide for 1 to 4 hours at 42° C. and then hybridize in the same solution with denatured labeled DNA probe and at 42° C. for overnight. After hybridization, wash the membrane with 0.2×SSPE, 0.1% SDS at 42° C. for 30 minutes and then wash in more stringent condition with 0.1×SSPE, 0.05%SDS at higher temperature, for example, at 55° C. for 30 minutes. Preferably, the polynucleotide is a DNA. More preferably, the DNA comprises a DNA encoding the polypeptide sequence of Table 1.

The present invention is further directed to a vector, comprising:

- a replicable vector; and
- the above-describe polynucleotide inserted into said vector.

The present invention is also directed to polypeptides encoded by the nucleic acid described above.

The present invention is related to a pharmaceutical composition comprising:

- a therapeutically effective amount of an inhibitor to the above described polypeptide; and
- a pharmaceutically acceptable carrier or diluent.

It is an object of the invention to provide a method of preventing tumor formation, comprising administering to a person in need thereof, a prophylactic amount of an inhibitor to human deoxycytidyl transferase. Preferably, the inhibitor blocks transcription or translation of the deoxycytidyl transferase gene. Also preferred is that the inhibitor blocks activity of the deoxycytidyl transferase protein by binding to the protein, in which case the preferred inhibitor is an antibody, more preferably, a monoclonal antibody.

Another object of the invention is to provide a method for treating or slowing metastasis of a tumor, comprising administering to a person in need thereof, a therapeutically effective amount of an inhibitor to human deoxycytidyl transferase.

Yet another object of the present invention is to provide a method for preventing mutations in a person, comprising administering to a person in need thereof, a therapeutically effective amount of an inhibitor to human deoxycytidyl transferase.

Table 1 describes the nucleotide and the deduced amino acid sequences of the human REV1 (hREV1) gene. Nucleotide sequence of the full-length hREV1 is shown in upper case letters while the 5' and the 3' nontranslated regions are shown in lower case letters. The deduced amino acid sequence is shown by the single letter symbols of amino acids. A mini open reading frame upstream of the hREV1 open reading frame is shown by the underline. The bold-type indicates the putative polyadenylation signal.

BRIEF DESCRIPTION OF THE DRAWINGS

The present invention will become more fully understood from the detailed description given hereinbelow, and the accompanying drawings which are given by way of illustration only, and thus are not limitative of the present invention, and wherein;

FIG. 3.—Conserved structural domain and sequence motifs of REV1 proteins from various biological sources. Several sequence features were identified by aligning REV1 protein sequences of various organisms as indicated. Identical amino acid residues are shaded. Similar amino acid residues are shown as "+" in the consensus sequence. Numbers in parentheses indicate gaps in the alignment. BRCT domain, the BRCA1 C-terminus domain; I–V, REV1 protein sequence motifs I to V. The REV1 sources are: ce, *C. elegans* (GenBank accession number Z46812); at, *A. thaliana* (GenBank accession number AC002342); sc, *S. cerevisiae* (GenBank accession number M22222); sp, *S. pombe* (GenBank accession number AL035548); h, *H. sapiens* (GenBank accession number AF151538).

ceRev1 BRCT domain is SEQ ID NO:10
ceRev1 sequence motif I is SEQ ID NO:11
ceRev1 sequence motif II is SEQ ID NO:12
ceRev1 sequence motif III is SEQ ID NO:13
ceRev1 sequence motif IV is SEQ ID NO:14
ceRev1 sequence motif V is SEQ ID NO:15
atRev1 BRCT domain is SEQ ID NO:16
atRev1 sequence motif I is SEQ ID NO:17
atRev1 sequence motif II is SEQ ID NO:18
atRev1 sequence motif III is SEQ ID NO:19
atRev1 sequence motif IV is SEQ ID NO:20
atRev1 sequence motif V is SEQ ID NO:21
scRev1 BRCT domain is SEQ ID NO:22
scRev1 sequence motif I is SEQ ID NO:23
scRev1 sequence motif II is SEQ ID NO:24
scRev1 sequence motif III is SEQ ID NO:25
scRev1 sequence motif IV is SEQ ID NO:26
scRev1 sequence motif V is SEQ ID NO:27
spRev1 BRCT domain is SEQ ID NO:28
spRev1 sequence motif I is SEQ ID NO:29
spRev1 sequence motif II is SEQ ID NO:30
spRev1 sequence motif III is SEQ ID NO:31
spRev1 sequence motif IV is SEQ ID NO:32
spRev1 sequence motif V is SEQ ID NO:33
hRev1 BRCT domain is SEQ ID NO:34
hREV1 sequence motif I is SEQ ID NO:35
hREV1 sequence motif II is SEQ ID NO:36
hREV1 sequence motif III is SEQ ID NO:37
hREV1 sequence motif IV is SEQ ID NO:38
hREV1 sequence motif V is SEQ ID NO:39

Figure 4:
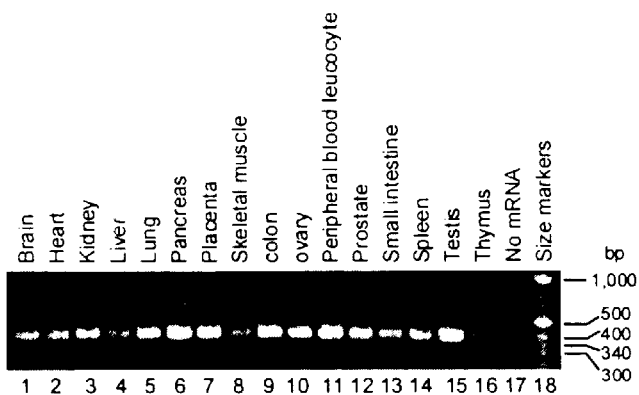

FIG. 4.—Expression of the REV1 gene in various human tissues. First strand cDNA was synthesized from polyA+ mRNA of various human tissues as indicated and normalized against the constitutive gene glyceraldehyde-3-phosphate dehydrogenase. A 360-bp DNA fragment corresponding to position +773 to +1132 of the human REV1 cDNA was amplified by 35 cycles of PCR as described in Materials and Methods. DNA products were separated by electrophoresis on a 1% agarose gel and visualized by ethidium bromide staining. The size markers in bp are shown on the right.

Figure 5:
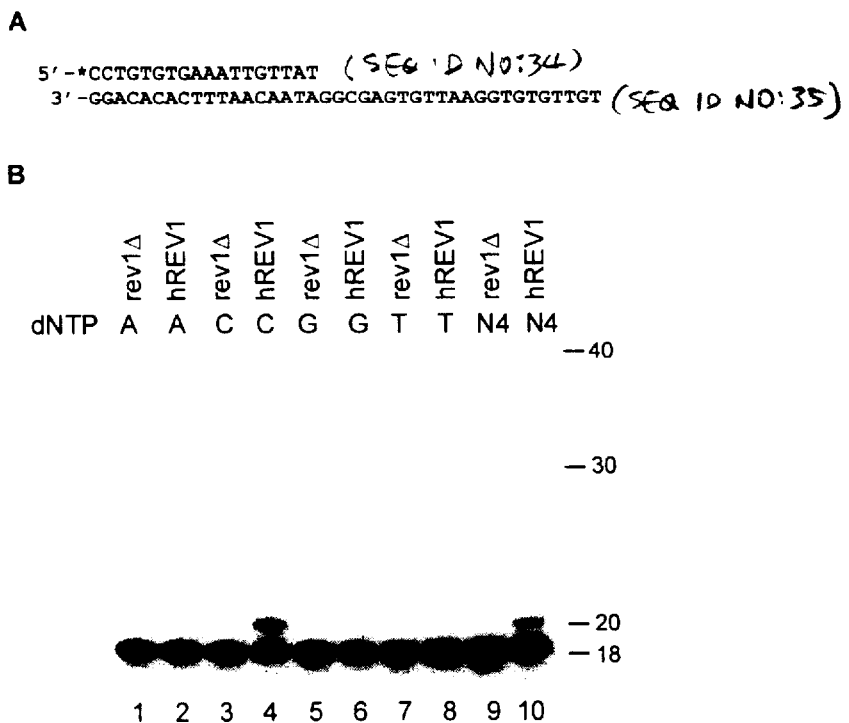

FIG. 5.—The dCMP transferase activity of the human REV1 protein. A. The DNA substrate used for dCMP transferase assays. The 18-mer primer was labeled with $^{32}$P at its 5' end. B. Standard dCMP transferase assays were performed in the reaction buffer containing a single dNTP (A, C, G, or T, lanes 1–8) or all four dNTPs (N4, lanes 9 and 10) as described in Material and Methods. Protein samples used were 2 μl of the partially purified human REV1 (lanes 2, 4, 6, 8, and 10), or 2 μl of an identically purified protein fraction from the rev1 deletion mutant cells (lanes 1, 3, 5, 7, and 9). DNA size markers in nucleotides are indicated on the right.

FIG. 6.—Transferase activity of the human REV1 protein opposite a template AP site. A. The DNA substrates used for dCMP transferase assays. The X position is a U without uracil-DNA glycosylase (UDG) treatment, or an AP site with UDG treatment. The 17-mer primer was labeled with $^{32}$P at its 5' end. B. Complete conversion of uracil-containing templates into AP site-containing templates. After converting the site-specific uracil residue into an AP site by UDG treatment (UDG, +), the template (0.4 pmol) was incubated with 500 ng of *E. coli* endonuclease III at 37° C. for 30 min (Endo III, +). Endo III cleaves DNA strand specifically at the AP site. The reaction products were separated by electrophoresis on a 15% native polyacrylamide gel and visualized by autoradiograpgy. Lanes 1 and 3 are controls without any treatment or with Endo III treatment only, respectively. C.

Standard dCMP transferase assays were performed with 2 μl of the partially purified human REV1 in the reaction buffer containing a single dNTP (A, C, G, or T, lanes 1–8) or all four dNTPs (N4, lanes 9 and 10) as described in Material and Methods. +UDG, AP site template; −UDG, uracil-containing template. Lanes 11 and 12, control experiments without dNTPs in the reaction mixtures. DNA size markers in nucleotides are indicated on the right.

Figure 7:
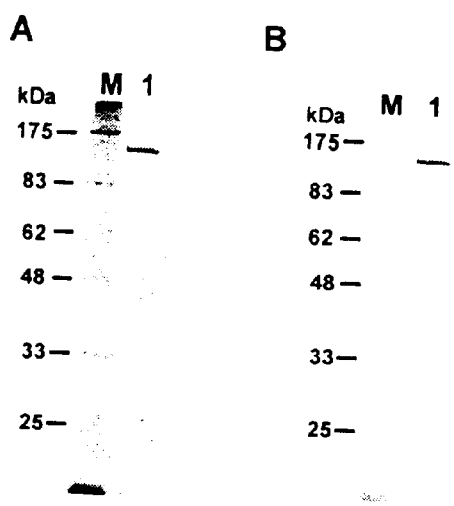

FIG. 7.—Pure human REV1 protein and its transferase activity. To confirm that the dCMP transferase activity is intrinsic to the human REV1, the protein was purified to apparent homogeneity as described in Materials and Methods. A. The most pure Mono Q fraction was separated by electrophoresis on a 10% SDS-polyacrylamide gel using 10 μl of the sample. The His-tagged human REV1 protein was visualized by silver staining. Protein size markers (lane M) in kDa are indicated on the left. B. The identity of the human REV1 protein was confirmed by Western blot using a monoclonal antibody against the His tag. C. A transferase assay was performed using the AP site-containing template (see FIG. 6A) without (lane 1) or with (lane 2) the pure human REV1 protein (2 μl, ~10 ng) in a reaction volume of 5 μl at 30° C. for 30 min. The reaction products were separated by electrophoresis on a 12% sequencing gel and visualized by autoradiography. DNA size markers in nucleotides are indicated on the right.

DETAILED DESCRIPTION OF THE INVENTION

DNA damage-induced mutagenesis is an important cellular response to unrepaired DNA lesions during replication. The biological outcome of this pathway is enhanced cell survival and increased mutations following DNA damage. The yeast *S. cerevisiae* has served as the most informative model organism in the studies of the damage-induced mutagenesis pathway in eukaryotes. Yeast genetic analyses have implicated at least 7 genes in this mutagenesis pathway, including REV1 (27).

Applicants have isolated a full-length cDNA of the yeast REV1 counterpart in humans. The REV1 protein is conserved from yeast to humans. Some regions share over 30% identity and more than 50% similarity between the yeast and the human proteins. The REV1 protein is additionally found in *S. pombe, C. elegans,* and *A. thaliana,* with significant sequence homologies among them. REV1 proteins of various sources all contain an N-terminal BRCT domain. It was originally identified in the breast cancer suppressor protein BRCA1 and subsequently found in some other proteins involved in cell cycle checkpoints, DNA repair, and recombination, such as Rad9, p53-binding protein, XRCC1, and DNA ligases III and IV (28–30). This structural domain is important in protein-protein interactions (31). Thus, it is likely that REV1 may interact with other proteins during damage-induced mutagenesis, although none of the REV1 interactions have been identified. Additionally, REV1 proteins contain several conserved sequence motifs (I–V), which closely resemble those of *E. coli* UmuC-related proteins (14).

Examination of the 5' untranslated region of the human REV1 cDNA revealed the presence of an out-of-frame ATG at nucleotide position −35 which initiates an ORF of 12 codons and terminates at position +2. The stop codon of this mini-ORF overlaps with the human REV1 initiator ATG codon. The sequence context of this upstream ATG is close to the consensus Kozak sequence (26). Thus, it is likely that the translational efficiency of the human REV1 message may be reduced by the presence of this upstream mini ORF.

Structural features of the human REV3 gene also suggest a low-level expression (21,22). These features imply that under normal growth conditions human cells may contain limited amounts of the mutagenesis proteins.

Most recently, by employing the yeast two-hybrid system Wixlerr et al. (32) identified a partial human cDNA whose polypeptide interacts with the cytoplasmic domain of the α3A integrin subunit. This cDNA clone (alpha integrin interacting protein 80, AIBP80) corresponds to the 2.6 kb of the 3' end of our human REV1 cDNA, with a few sequence discrepancies. This sequence was localized by the Sanger Centre between 2q11.1 and 2q11.2, a region identical to Applicants' human REV1 chromosomal location.

Applicants found that the human REV1 protein is a dCMP transferase capable of inserting a dCMP opposite a template AP site. This activity provides evidence supporting a role of the REV1 protein in damage-induced mutagenesis in humans. In vitro, the human REV1 dCMP transferase functions efficiently opposite a template AP site. Thus, the human REV1 transferase may play a critical role during mutagenic translesion DNA synthesis opposite a template AP site in vivo. Supporting this notion, Johnson et al. (33) recently demonstrated that AP site-induced mutagenesis in yeast requires the Rev1 protein. The results presented herein also suggest that the damage-induced mutagenesis pathway will incorporate a C residue opposite an AP site during human DNA replication, regardless of the original base identity previously residing at the AP site. Since REV1 is also needed for UV-induced mutagenesis in yeast (27), additional function of the protein must be involved during mutagenesis opposite other DNA lesions.

Yeast Rev1 is also a dCMP transferase (15). Thus, detection of the dCMP transferase activity of the human REV1 indicates that it is both a structural and a functional homologue of the yeast protein. Additionally, humans contain highly conserved homologues of the yeast mutagenesis proteins Rad6 (19,20) and Rev3 (21,22). Taken together, these observations clearly indicate the existence of a damage-induced mutagenesis pathway in humans in response to DNA lesions. Further supporting this conclusion, Gibbs et al (21) showed that UV-induced mutagenesis in human cells requires the human REV3. The damage-induced mutagenesis pathway is likely a fundamental and major mechanism for generating mutations in humans after DNA damage. Consistent with this hypothesis, ubiquitous expression for both REV1 and REV3 (22) in various human tissues was observed.

Abbreviations

Abbreviations for amino acids used herein are conventionally defined as described hereinbelow unless otherwise indicated.

| Amino Acid | Three-letter abbreviation | One-letter symbol |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Diaminopropionic acid | Dpr | |
| Glutamine | Gln | Q |
| Glutamic acid | Glu | E |

-continued

| Amino Acid | Three-letter abbreviation | One-letter symbol |
| --- | --- | --- |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Ornithine | Orn | |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Specifically Exemplified Polypeptides

The present invention relates to polypeptides comprising the sequences exemplified in Table 1. The polypeptide can be prepared by isolation from natural sources, polypeptide synthesis by known synthetic methods, or expression and recovery from a recombinant organism or by any other convenient method.

Variants of Polypeptide

Variants of the specifically exemplified polypeptides are also encompassed by the present invention. Possible variants include allelic variants and corresponding polypeptides from other organisms, particularly other organisms of the same species, genus or family. The variants may have substantially the same characteristics as the natural polypeptides. The variant polypeptide will possess one or more or all of the following physical and/or biological properties. Physical properties: ~140 kDa as determined by electrophoresis on a 10% SDS-polyacrylamide gel. Biological properties: deoxycytidyl transferase activity of the polypeptide that catalyzes the insertion of a dCMP to a DNA primer opposite a template G residue or a template apurinic/apyrimidinic (AP) site as determined by a primer extension assay.

Primer extension assay: a DNA template or a DNA oligonucleotide annealed with a $^{32}$P-labeled DNA primer right before the template G residue or the template AP site. Incubation of this DNA substrate with the polypeptide containing a dCMP transferase activity under a standard DNA polymerase assay buffer will extend the labeled primer one nucleotide longer which is detected by a sequencing gel. Inactivation or inhibiting this polypeptide through chemical, biochemical, or molecular techniques will lead to inhibition of mutagenesis induced by ultraviolet (UV) and possibly some other DNA damaging agents. Mutagenesis is determined by a standard mutation assay in human cells such as the HPRT forward mutation assay measuring mutations that confer cells resistance to 6-thioguanine (Quan, T., Reiners, J. J., Jr., Culp, S. J., Richter, P., and States, J. C. (1995) *Mol. Carcinog.* 12, 91–102).

Substitutions, Additions and Deletions

As possible variants of the above specifically exemplified polypeptides, the polypeptide may have additional individual amino acids or amino acid sequences inserted into the polypeptide in the middle thereof and/or at the N-terminal and/or C-terminal ends thereof so long as the polypeptide possesses the desired physical and/or biological characteristics. Likewise, some of the amino acids or amino acid sequences may be deleted from the polypeptide so long as the polypeptide possesses the desired physical characteristics. Amino acid substitutions may also be made in the sequences so long as the polypeptide possesses the desired physical and biochemical characteristics.

Sequence Identity at the Amino Acid Level

The variants of polypeptides contemplated herein should possess more than 75% sequence identity (sometimes referred to as homology, preferably more than 85% identity, most preferably more than 95% identity, even more preferably more than 98% identity to the naturally occurring and/or specifically exemplified polypeptides or fragments thereof described herein. To determine this homology, two polypeptides are aligned so as to obtain a maximum match using gaps and inserts.

Two sequences are said to be "identical" if the sequence of residues is the same when aligned for maximum correspondence as described below. The term "complementary" applies to nucleic acid sequences and is used herein to mean that the sequence is complementary to all or a portion of a reference polynucleotide sequence.

Optimal alignment of sequences for comparison can be conducted by the local homology algorithm of Smith and Waterman, *Add. Appl. Math.*, 2:482 (1981), by the homology alignment method of Needleman and Wunsch, *J. Mol. Biol.*, 48:443 (1970), by the search for similarity method of Pearson and Lippman, *Proc. Natl. Acad. Sci. USA*, 85:2444 (1988), or the like. Computer implementations of the above algorithms are known as part of the Genetics Computer Group (GCG) Wisconsin Genetics Software Package (GAP, BESTFIT, BLASTA, FASTA and TFASTA), 575 Science Drive, Madison, Wis.

"Percentage of sequence identity" is determined by comparing two optimally aligned sequences over a comparison window, wherein the portion of the sequence in the comparison window may comprise additions or deletions (i.e. "gaps") as compared to the reference sequence for optimal alignment of the two sequences being compared. The percentage identity is calculated by determining the number of positions at which the identical residue occurs in both sequences to yield the number of matched positions, dividing the number of matched positions by the total number of positions in the window and multiplying the result by 100 to yield the percentage of sequence identity. Total identity is then determined as the average identity over all of the windows that cover the complete query sequence.

Post-translational Modification

Also included within the scope of the present invention are polypeptides or fragments or derivatives thereof which are differentially modified during or after translation, e.g., by glycosylation, proteolytic cleavage, phosphorylation, methylation, and amidation of glutamic acid, aspartic acid and C-terminal carboxyl groups, lipid modification, such as prenylation and palmitoylation, and acetylation of the N-terminus.

Fusion Polypeptides

The polypeptide of the present invention may be expressed as a fusion polypeptide or chimeric polypeptide with a second polypeptide. The second polypeptide will usually impart an additional property or characteristic to the fusion polypeptide which is not possessed by the polypeptide of the present invention.

Fragments of Polypeptide

Fragments of the full length polypeptides such as proteolytic cleavage fragments which contain at least one, and preferably all, of the above-listed physical and/or biological properties are also encompassed by the present invention.

The polypeptide or fragment or variant thereof usually has a length of at least about 100 amino acids, usually less than 1,300 amino acids, preferably between 500 and 1,300 amino acids, more preferably between 500 and 900 amino acids. Significantly featured regions: the BRCT domain from amino acid 48 to amino acid 140 of the human REV1 protein may be involved in interactions with other proteins.

REV1 motif I from amino acid 344 to amino acid 380 of the human REV1 protein may be involved in the catalytic activity of the REV1 protein.

REV1 motif II from amino acid 415 to amino acid 450 of the human REV1 protein may be involved in the catalytic activity of the REV1 protein.

REV1 motif III from amino acid 523 to amino acid 570 of the human REV1 protein may be involved in the catalytic activity of the REV1 protein.

REV1 motif IV From amino acid 580 to amino acid 620 of the human REV1 protein may be involved in the catalytic activity of the REV1 protein.

REV1 motif V from amino acid 621 to amino acid 662 of the human REV1 protein may be involved in the catalytic activity of the REV1 protein. All of these regions are shown in FIG. 3.

Production of Recombinant Polypeptide

The present invention is also directed to a new polypeptide and a method for producing the polypeptide. The recombinant polypeptide should possess one or more of the above-described biological and/or physical properties.

Recombinant polypeptide can be produced by a process which comprises culturing the transformed cell or microorganism described herein under conditions which allow expression of the polypeptide, optionally recovering the thus expressed polypeptide and optionally purifying the recovered polypeptide. In the processes for the synthesis of the polypeptide, DNA which encodes the polypeptide is ligated into a replicable (reproducible) vector, the vector is used to transform host cells, and the polypeptide is recovered from the culture. Suitable replicable vectors will be selected depending upon the particular host cell chosen. Suitable processes are known in the art and are described, for example, in Sambrook et al, Molecular Cloning: A Laboratory Manual, 2nd Ed. c. 1989 by Cold Spring Harbor Laboratory Press, Cold Spring Harbor, N.Y., Chapters 16, 17 and 18.

The polypeptide produced in this manner may be different from natural polypeptide in that it may be free of other polypeptides or materials which occur in natural polypeptide. The polypeptide produced by recombinant techniques may also contain some small amounts of contaminating materials from the microorganism, cells and/or fermentation system in which it was produced. Thus, the present invention is also directed to these new or isolated polypeptides which are produced by recombinant DNA techniques.

Purification of Recombinant Polypeptide

Recombinant polypeptide can be recovered from cultures by lysing the cells to release recombinant polypeptide which is present inside the cells. Initially, cell debris can be separated by centrifugation. The remaining debris and the supernatant are then repeatedly treated with solvents in which the cell debris are soluble but in which the recombinant polypeptide is not soluble to thereby precipitate recombinant polypeptide. These procedures can be repeated and combined with other procedures including filtration, dialysis and/or chromatography to obtain a pure product.

DNA and RNA

The invention encompasses DNA that codes for any one of the above-described polypeptides including, but not limited to, those shown in Table 1, including fusion polypeptides, variants and fragments thereof. The sequence of the cDNA which has actually been sequenced is shown in Table 1. The present invention also includes cDNA as well as genomic DNA containing or comprising the requisite nucleotide sequences as well as corresponding RNA and antisense sequences.

Cloned DNA within the scope of the invention also includes allelic variants of the specific sequences presented in Table 1. An "allelic variant" is a sequence that is a variant from that of the exemplified nucleotide sequence, but represents the same chromosomal locus in the organism. In addition to those which occur by normal genetic variation in a population and perhaps fixed in the population by standard breeding methods, allelic variants can be produced by genetic engineering methods. A preferred allelic variant is one that is found in a naturally occurring organism, including a laboratory strain. Allelic variants are either silent or expressed. A silent allele is one that does not affect the phenotype of the organism. An expressed allele results in a detectable change in the phenotype of the trait represented by the locus.

A nucleic acid sequence "encodes" or "codes for" a polypeptide if it directs the expression of the polypeptide referred to. The nucleic acid can be DNA or RNA. Unless otherwise specified, a nucleic acid sequence that encodes a polypeptide includes both the transcribed strand and the mRNA or the DNA representative of the mRNA. An "antisense" nucleic acid is one that is complementary to a strand representative of mRNA, including untranslated portions thereof.

Degenerate Sequences

In accordance with degeneracy of genetic code, it is possible to substitute at least one base of the base sequence of a gene by another kind of base without causing the amino acid sequence of the polypeptide produced from the gene to be changed. Hence, the DNA of the present invention may also have any base sequence that has been changed by substitution in accordance with degeneracy of genetic code.

DNA Modification

The DNA is readily modified by substitution, deletion or insertion of nucleotides, thereby resulting in novel DNA sequences encoding the polypeptide or its derivatives. These modified sequences are used to produce mutant polypeptide and to directly express the polypeptide. Methods for saturating a particular DNA sequence with random mutations and also for making specific site directed mutations are known in the art; see e.g. Sambrook et al supra, Chapter 15.

Hybridizable Variants

The DNA molecule can comprise a nucleotide sequence as shown in Table 1, or can comprise a nucleotide sequence selected from the group consisting of a nucleotide sequence that hybridizes to a DNA molecule encoding the amino acid sequence shown in Table 1 under salt and temperature conditions equivalent to 5×SSC and 42° C. Preferably, the DNA molecule is prehybridized in solution of 5×SSPE, 5×denhardt's and 0.5%SDS, 50% formamide, 20–100 µg/ml sonicated non-homologous DNA for 1 to 4 hours at 42° C., and then hybridized in the same solution but without non-homologous DNA and with denatured labeled DNA probe for overnight at 42° C. After hybridization, the filter is washed twice under less stringent conditions such as in 2×SSPE, 0.1%SDS for 10 minutes at 42° C., a more stringent condition is as follows: Prehybridization, hybridization and less stringent wash are the same as above, but a more stringent wash condition is used such as: wash in 1×SSPE, 0.1%SDS at 60° C. for 10 to 30 minutes and then in 0.1×SSPE, 0.1%SDS at 60° C. for 10 minutes if necessary. The hybridized DNA codes for a polypeptide that has one or more or all of the above-described physical and/or biological properties. The present invention also includes polypeptides coded for by these hybridizable variants. See Chapters 11 and 12 of Sambrook et al, supra.

Recombinant DNA Constructs

Recombinant DNA constructs comprising one or more of the DNA or RNA sequences described herein and an additional DNA and/or RNA sequence are also included within the scope of this invention. These recombinant DNA constructs have sequences which do not occur in nature or exist in a form that does not occur in nature or exist in association with other materials that do not occur in nature. The DNA and/or RNA sequences described hereinabove are "operably linked" with other DNA and/or RNA sequences. DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous (or in close proximity to) and, in the case of secretory leaders, contiguous and in reading phase.

Vectors

The invention is further directed to a replicable vector containing cDNA which codes for the polypeptide and which is capable of expressing the polypeptide.

The present invention is also directed to a vector comprising a replicable vector and a DNA sequence corresponding to the above described gene inserted into said vector. The vector may be an integrating or non-integrating vector and is conveniently a plasmid.

Transformed Cells

The invention further relates to a transformed cell or microorganism containing cDNA or a vector which codes for the polypeptide or a fragment or variant thereof and which is capable of expressing the polypeptide.

Prokaryotic Host-Vector Systems

A plethora of suitable microbial vectors are available. Generally, a microbial vector will contain an origin of replication recognized by the intended host, a promoter which will function in the host and a phenotypic selection gene, for example, a gene encoding proteins conferring antibiotic resistance or supplying an auxotrophic requirement.

Vectors must contain a promoter which is recognized by the host organism. This is generally a promoter homologous to the intended host. Promoters often used in recombinant DNA construction include the β-lactamase (penicillinase) and lactose promoter systems, a tryptophan (trp) promoter system and the tac promoter. While these are commonly used, other known microbial promoters are suitable. Details concerning their nucleotide sequences have been published, enabling a skilled worker to operably ligate them to DNA encoding the desired polypeptide in plasmid vectors and the DNA encoding the desired polypeptide. At the present time a preferred vector is pGEX vector with tac promotor, pRSET vector with T7 promotor, or pET vector with T7 promotor. Other possible expression vectors are pTrc vector with trc promotor, pBAD vector with BAD promotor, pPROLar.A and pPROTet.E vector, and pRIT2T vector.

Common prokaryotic host cells include bacteria such as $E.\,coli$.

Expression Systems Using Yeast Cells

In addition to prokaryotes, eukaryotic microbes such as yeast cultures may be transformed with polypeptide encoding vectors. Saccharomyces cerevisiae, or common baker's yeast, is commonly used among lower eukaryotic host microorganisms, although a number of other strains are commonly available. Yeast vectors generally will contain an origin of replication from the 2 micron yeast plasmid or an autonomously replicating sequence (ARS), a promoter, a DNA sequence coding for the desired polypeptide, sequences for polyadenylation and transcription termination and a selection gene.

Suitable promoting sequences in yeast vectors include the promoters for metallothionein, 3-phosphoglycerate kinase or other glycolytic enzymes.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes are also ligated into the expression vector 3' of the polypeptide coding sequences to provide polyadenylation of the mRNA and termination.

Expression Systems Using Vertebrate Cells

Interest has been great in vertebrate cells, and propagation of vertebrate cells in culture (tissue culture) has become a routine procedure. Examples of useful mammalian host cell lines are VERO and HeLa cells, Chinese hamster ovary (CHO) cell lines, and WI38, BHK, COS-7 and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and most preferably Simian Virus 40 (SV40). The early and late promoters are particularly useful because both are obtained easily from the virus as a fragment which also contains the SV40 viral origin of replication. Smaller or larger SV40 fragments may also be used, provided the approximately 250 bp sequence extending from the Hind III site toward the BglI site located in the viral origin of replication is included.

An origin of replication may be provided either by construction of the vector to include an exogenous origin, such as may be derived from SV40 or other viral (e.g., Polyoma, Adenovirus, VSV, or BPV) source, or may be provided by the host cell chromosomal replication mechanism. If the vector is integrated into the host cell chromosome, the latter is often sufficient.

Insect Cell Expression Systems

Insect cell expression systems can be used with the present invention, as they are commonly described in Ausubel et al., *Current Protocols in Molecular Biology*, Green and Wiley, pub.(1994), which is incorporated herein by reference in its entirety.

Plant Cell Expression Systems

Plant Vectors

In plants, transformation vectors capable of introducing nucleic acid encoding deoxycytidyl (dCMP) transferase are easily designed, and generally contain one or more DNA coding sequences of interest under the transcriptional control of 5' and 3' regulatory sequences. Such vectors generally comprise, operatively linked in sequence in the 5' to 3' direction, a promoter sequence that directs the transcription of a downstream heterologous structural DNA in a plant; optionally a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding said protein. Plant transformation vectors also generally contain a selectable marker. Typical 5'-3' regulatory sequences include a transcription initiation start site, a ribosome binding site, an RNA processing signal, a transcription termination site, and/or a polyadenylation signal.

Plant Promoters

Plant promoter sequences can be constitutive or inducible, environmentally- or developmentally-regulated, or cell- or tissue-specific. Often-used constitutive promoters include the CaMV 35S promoter, the enhanced CaMV 35S promoter, the Figwort Mosaic Virus (FMV) promoter, the mannopine synthase (mas) promoter, the nopaline synthase (nos) promoter, and the octopine synthase (ocs) promoter. Useful inducible promoters include heat-shock promoters, a nitrate-inducible promoter derived from the spinach nitrate reductase gene, hormone-inducible promoters, and light-inducible promoters associated with the small subunit of RuBP carboxylase and LHCP gene families. Examples of useful tissue-specific, developmentally regulated promoters include the β-conglycinin 7S promoter and seed-specific promoters. Plant functional promoters useful for preferential expression in seed plastics include those from plant storage protein genes and from genes involved in fatty acid biosynthesis in oilseeds. Examples of such promoters include the 5'-regulatory regions from such genes as napin, phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Hoffman, U.S. Pat. No. 5,106,739), or to combine desired transcriptional activity and tissue specificity.

Plant Transformation and Regeneration

A variety of different methods can be employed to introduce such vectors into plant protoplasts, cells, callus tissue, leaf discs, meristems, etc., to generate transgenic plants, including Agrobacterium-mediated transformation, particle gun delivery, microinjection, electroporation, polyethylene glycol-mediated protoplast transformation, liposome-mediated transformation, etc. In general, transgenic plants comprising cells containing and expressing DNAs encoding deoxycytidyl transferase can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the enzyme-encoding nucleotide sequence.

The encoding DNAs can be introduced either in a single transformation event (all necessary DNAs present on the same vector), a co-transformation event (all necessary DNAs present on separate vectors that are introduced into plants or plant cells simultaneously), or by independent transformation events (all necessary DNAs present on separate vectors that are introduced into plants or plant cells independently). Traditional breeding methods can subsequently be used to incorporate the entire pathway into a single plant. Specific methods for transforming a wide variety of dicots and obtaining transgenic plants are well documented in the literature.

Successful transformation and plant regeneration have been achieved in the monocots as follows: asparagus (*Asparagus officinalis;* Bytebier et al, Proc. Natl. Acad. Sci. USA, 84:5345 (1987)); barley (*Hordeum vulgarae;* Wan and Lemaux, Plant Physiol., 104:37 (1994)); maize (*Zea mays;* Rhodes et al, Science, 240:204 (1988); Gordon-Kamm et al, Plant Cell, 2:603 (1990); Fromm et al, Bio/Technology, 8:833 (1990); Koziel et al, Bio/Technology, 11:194 (1993)); oats (*Avena saliva;* Somers et al, Bio/Technology, 10:1589 (1992)); orchardgrass (*Dactylic glomerata;* Horn et al, Plant Cell Rep., 7:469 (1988)); rice (*Oryza saliva,* including indica and japonica varieties; Toriyama et al, Bio/Technology, 6:10 (1988); Zhang et al, Plant Cell Rep., 7:379 (1988); Luo and Wu, Plant Mol. Biol. Rep., 6:165 (1988); Zhang and Wu, Theor. Appl. Genet., 76:835 (1988); Christou et al, Bio/Technology, 9:957 (1991)); rye (*Secale cereale;* De la Pena et al, Nature, 325:274 (1987)); sorghum (*Sorghum bicolor;* Cassas et al, Proc. Natl. Acad. Sci. USA; 90:11212 (1993)); sugar cane (Saccharum spp.; Bower and Birch, Plant J., 2:409 (1992)); tall fescue (*Festuca arundinacea;* Wang et al, Bio/Technology, 10:691 (1992)); turf-grass (*Agrostis palustris;* Zhong et al, Plant Cell Rep., 13:1 (1993)); and wheat (*Triticum aestinum;* Vasil et al, Bio/Technology, 10:667 (1992); Weeks et al, Plant Physiol., 102:1077 (1993); Becker et al, Plant J., 5:299 (1994)).

Production of Transgenic Plants Comprising Genes for Deoxycytidyl Transferase

Plant transformation vectors capable of delivering DNAs (genomic DNAs, plasmid DNAs, cDNAs, or synthetic DNAs) encoding deoxycytidyl transferase can be easily designed. Various strategies can be employed to introduce these encoding DNAs to produce transgenic plants capable of biosynthesizing high levels of deoxycytidyl transferase including:

1. Transforming individual plants with an encoding DNA of interest. Two or more transgenic plants, each containing one of these DNAs, can then be grown and cross-pollinated so as to produce hybrid plants containing the two DNAS. The hybrid can then be crossed with the remaining transgenic plants in order to obtain a hybrid plant containing all DNAs of interest within its genome.
2. Sequentially transforming plants with plasmids containing each of the encoding DNAs of interest, respectively.
3. Simultaneously cotransforming plants with plasmids containing each of the encoding DNAs, respectively.
4. Transforming plants with a single plasmid containing two or more encoding DNAs of interest.
5. Transforming plants by a combination of any of the foregoing techniques in order to obtain a plant that expresses a desired combination of encoding DNAs of interest.

Traditional breeding of transformed plants produced according to any one of the foregoing methods by successive rounds of crossing can then be carried out to incorporate all the desired encoding DNAs in a single homozygous plant line (Nawrath et al, 1994; PCT International Publication WO 93/02187).

In methods 2 and 3, the use of vectors containing different selectable marker genes to facilitate selection of plants containing two or more different-encoding DNAs is advantageous. Examples of useful selectable marker genes include those conferring resistance to kanamycin, hygromycin, sulphonamides, glyphosate, bialaphos, and phosphinothricin.

Stability of Transgene Expression

As several overexpressed enzymes may be required to produce optimal levels of deoxycytidyl transferase, the phenomenon of co-suppression may influence transgene expression in transformed plants. Several strategies can be employed to avoid this potential problem.

One commonly employed approach is to select and/or screen for transgenic plants that contain a single intact copy of the transgene or other encoding DNA. Agrobacterium-mediated transformation technologies are preferred in this regard.

Inclusion of nuclear scaffold or matrix attachment regions (MAR) flanking a transgene has been shown to increase the level and reduce the variability associated with transgene expression in plants. Flanking a transgene or other encoding DNA with MAR elements may overcome problems associated with differential base composition between such transgenes or encoding DNAs and integration sites, and/or the detrimental effects of sequences adjacent to transgene integration sites.

The use of enhancers from tissue-specific or developmentally-regulated genes may ensure that expression of a linked transgene or other encoding DNA occurs in the appropriately regulated manner.

The use of different combinations of promoters, plastid targeting sequences, and selectable markers for introduced transgenes or other encoding DNAs can avoid potential problems due to trans-inactivation in cases where pyramiding of different transgenes within a single plant is desired.

Finally, inactivation by co-suppression can be avoided by screening a number of independent transgenic plants to identify those that consistently overexpress particular introduced encoding DNAs. Site-specific recombination in which the endogenous copy of a gene is replaced by the same gene, but with altered expression characteristics, should obviate this problem.

Any of the foregoing methods, alone or in combination, can be employed in order to insure the stability of transgene expression in transgenic plants of the present invention.

Immunization of Mice and Isolation of Polyclonal Antibodies

Antibodies to hREV1 are made using conventional methods, such as discussed in Ausubel et al. *Current Protocols in Molecular Biology*, Vol. 2, Supplement 18, Greene publishing and John Wiley & Sons (1994), which is incorporated herein by reference in its entirety. An example of how the antibodies are made is as follows. Female B6SJLF$_1$/J (Jackson Labs), approximately 8 weeks of age, are immunized with hREV1 immunogen which has been dissolved in PBS and emulsified with an equal volume of complete Freund's adjuvant. Using two groups of five mice each, immunization is performed by intraperitoneal injection of 50.0 μg of hREV1 (with adjuvant) in a final volume of 0.2 ml PBS. At 4 weeks and 8 weeks post initial injection, each mouse receives an identical quantity of hREV1 emulsified with incomplete Freund's adjuvant. Approximately 10 days after the second injection, serum sample are taken from each mouse via the retro-orbital sinus and are assayed for anti-hREV1 antibody activity by competitive ELISA immunoassay determination. For those mice showing the presence of specific antibody in their serum, each is given a final immunization of the identical hREV1 again in 0.1 ml of PBS injected into the tail vein 3 days prior to sacrifice of the animal.

The competitive ELISA immunoassay also is used to determine the presence of specific antibodies against hREV1 in mouse sera (and subsequently to identify specific hybridomas); these assays are modifications of methods previously described in the art (Haugen et al., *Proc. Natl. Acad. Sci. U.S.A.* 78:4124–4127 (1981); Groopman et al., *Cancer Res.* 42:3120–3124 (1982)). Briefly summarizing the procedure, hREV1 is dissolved in PBS at a concentration of 2.0 μg/ml and 50 μl of this fluid mixture is added to each well of a polyvinyl microtiter plate and allowed to incubate for 2–4 hours at ambient temperature. Other wells in the microtiter plate receive 50 μl of gelatin in PBS at a concentration of 2 μg/ml and serve as controls. The fluid in each well is then aspirated and each well is washed 3 times with PBS with 0.05% (vol/vol) TWEEN 20. Subsequently, each well receives a PBS solution containing 0.2% gelatin and the plates are allowed to incubate for an additional hour at ambient temperature. This procedure is designed to limit non-specific binding of antibodies. The plates are then washed in PBS with 0.05% TWEEN 20 and 50 μl aliquots of diluted mouse serum samples (or hybridoma medium) plus appropriate competitor are added to each well. To titer the mouse sera, dilutions in PBS with 0.05% TWEEN 20 are prepared over a range from 1:100–1:51,200 in continuing two-fold dilutions. The microtiter plates are then incubated for 90 minutes at 37° C., after which they are thoroughly washed with PBS+0.05% TWEEN 20. Specific antibodies that become bound to the surface of each well are detected by adding 50 μl of a 1:1000 dilution of goat anti-mouse IgG+IgM antibody coupled to alkaline phosphatase to each well followed by incubation of 90 minutes at 37° C. The wells in each plate are then rewashed with PBS with TWEEN 20 plus a final wash with tap water. 100 μl per well of 1.0 mg/ml p-nitrophenyl phosphate solution (Sigma) prepared in 0.1M diethanolamine buffer, pH 9.8 then is added and allowed to react for 30 min. Quantitative measurement of the p-nitrophenol reaction product is performed by measuring the absorbance of the assay well at 405 nanometers using a microtiter plate reader (Dynatech Labs).

The isotypes of the monoclonal antibodies (that is the determination and identification of different antibody heavy chain class) are determined in a non-competitive ELISA methodology using a commercially purchased kit for mouse immunoglobulin subtype identification (Boeringer-Mannheim Company).

Preparation of Hybridomas and Isolation of Monoclonal Antibody Producing Cells

Hybridomas and monoclonal antibodies to hREV1 are prepared using conventional methods, such as discussed in Ausubel et al. *Current Protocols in Molecular Biology*, Vol. 2, Supplement 18, Green Publishing and John Wiley & Sons (1994), which is incorporated herein by reference in its entirety. An example of how the hybridomas and monoclonal antibodies are made is as follows. The female B6SJLF$_1$/J mice previously immunized with hREV1 in complete Freund's adjuvant are tested for production of significant anti-hREV1 serum titers using the competitive ELISA methodology as described above. Those mice showing high titers are sacrificed and hybridomas prepared following the procedures previously described in Marshak-Rothstein et al., *J. Immun.*, 122:2491–2497 (1979). The myeloma cell line used for cell fusion are P3-X63/Ag8.653 cells which were maintained in Dulbecco's Modified Eagles medium (hereinafter "DME" medium) supplemented with 20% (volume/volume) fetal calf serum, 2 mM L-Glutamine, 10 units/ml penicillin, 100 μg/ml streptomycin, and nonessential amino acids (Gibco). The mice are sacrificed and spleen cell suspensions prepared using Hanks' balance salt solution buffered with 0.01M phosphate, pH 7.2 (hereinafter "HPBS").

The spleen cells from these mice are fused with P3-X63/Ag8.653 myeloma cells using a modification of the Gefter et al. procedure (*Somatic Cell Genet.* 3:321 (1977)). Unless stated otherwise, all centrifugations are preformed at 700 times gravity for 5 minutes at room temperature. Preferably, $5 \times 10^6$ P3-X63/Ag8.653 myeloma cells and $2.5 \times 10^7$ immune spleen cells are combined in a round bottom plastic tube, centrifuged, resuspended in 10 ml of serum free DME medium and centrifuged again. The supernatant is carefully discarded and the centrifuge tube tapped sharply to disperse the residual cell pellet. The cells are then exposed to 0.5 ml of a 30% (volume/volume) solution of polyethylene glycol 1000 (Baker Chemical Company) in serum free DME for 6 minutes. During this 6 minute period, the cell suspension is gently centrifuged (150×gravity for 3 minutes). 4.0 ml of serum free DME is then added to the cell pellet and the cells again resuspended by tapping the tube. The contents of the tube are transferred to 100×17 mm Petri dishes and cultured in DME medium containing 20% fetal calf serum for 1 day. The cells are then centrifuged again and resuspended in growth medium containing hypoxanthine, aminopterin and thymidine (hereinafter "HAT medium"). 0.1 ml aliquots of the cells are then distributed into the wells of flat bottom microtiter dishes, each aliquot containing approximately $10^5$ P3-X63/Ag8.653 cells. After one week's incubation, 0.05 ml of growth medium containing only hypoxanthine and thymidine (hereinafter "HT medium") is added to each well. Cultures are screened for specific anti-hREV1 antibody activity two weeks post fusion using the competitive ELISA immunoassay technique described earlier.

Hybridomas secreting monoclonal antibodies of high affinity specific for hREV1 are grown as ascites tumor cells in Scid mice which has been previously injected with 0.5 ml pristane (Aldrich). The hybridomas growing within the mice produce large quantities of specific monoclonal antibodies which are harvested and collected as ascites fluid from each mouse before it dies. The collected fluid from these animals is pooled and either used directly in the immunoassays or further purified by saturated ammonium sulfate precipitation and dialysed against PBS. Gross pathological examination shows that all mice die as a result of widespread tumor invasion—that is growth of the injected hybridoma cells.

Utility

The gene or DNA of the present invention and the polypeptide which is coded by the DNA of the present invention have various potential uses.

1. It is possible that the polypeptide of the present invention is useful as a deoxycytidyl transferase. Thus, if the polypeptide of the present invention is introduced into or contacted with a cell, it will cause a specific mutagenic bypass opposite an abasic site.
2. A drug might exist or might be developed which specifically enhances or inhibits the function of this polypeptide. Knowledge of the precise sequence bound by the polypeptide provides an obvious approach to targeted drug therapy.
3. It is also possible that an anti-sense sequence which binds to single stranded RNA corresponding to the gene of the present invention could be made whereby the anti-sense sequence would bind to single stranded RNA to prevent expression of the polypeptide.

Therapeutic Uses

In the practice of the therapeutic methods of the present invention, an effective amount of the active compound, including derivatives or salts thereof, or a pharmaceutical composition containing the same, as described below, is administered via any of the usual and acceptable methods known in the art, either singly or in combination with another compound or compounds of the present invention or other pharmaceutical agents such as immunosuppressants, antihistamines, corticosteroids, and the like. These compounds or compositions can thus be administered orally, sublingually, topically (e.g., on the skin or in the eyes), by inhalation or by suppository, parenterally (e.g., intramuscularly, intravenously, subcutaneously or intradermally), or by inhalation, and in the form of either solid or liquid dosage including tablets, suspensions, and aerosols, as is discussed in more detail below. The administration can be conducted in single unit dosage form with continuous therapy or in single dose therapy ad libitum. A unit dose is defined as 1 to 3000 mg for a human patient.

Useful pharmaceutical carriers for the preparation of the pharmaceutical compositions hereof can be solids, liquids or mixtures thereof; thus, the compositions can take the form of tablets, pills, capsules, powders, enterically coated or other protected formulations (such as binding on ion exchange resins or other carriers, or packaging in lipid or lipoprotein vesicles or adding additional terminal amino acids), sustained release formulations, erodible formulations, implantable devices or components thereof, microsphere formulations, solutions (e.g., ophthalmic drops), suspensions, elixirs, aerosols, and the like.

Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in Martin, "Remington's Pharmaceutical Sciences", 15th Ed.; Mack Publishing Co., Easton (1975); see, e.g., pp. 1405–1412 and pp. 1461–1487. Such compositions will, in general, contain an effective amount of the active compound together with a suitable amount of carrier so as to prepare the proper dosage form for proper administration to the host.

In one preferred embodiment, the therapeutic methods of the present invention are practiced when the relief of symptoms is specifically required or perhaps imminent; in another preferred embodiment, the method hereof is effectively practiced as continuous or prophylactic treatment.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range of 0.1 to 100 mg of compound per kilogram of subject body weight will be useful, and a range of 1 to 100 mg per kg generally preferred, where administration is by injection or ingestion. Topical dosages may utilize formulations containing generally as low as 0.1 mg of compound per ml of liquid carrier or excipient, with multiple daily applications being appropriate.

The invention being thus described, it is obvious that the same can be varied in many ways. Such variations are not to be regarded as a departure from the spirit and scope of the present invention, and all such modifications as would be obvious to one skilled in the art are intended to be included within the scope of the following claims.

EXAMPLES

Materials and Methods

Materials

Human bone marrow and leukocyte cDNA libraries in λgt11 were purchased from Clontech Laboratories. A human T cell cDNA library in the ZAP Express vector and a human placenta genomic DNA library were purchased from Stratagene. E. coli uracil-DNA glycosylase was obtained from New England BioLabs. The vector pUC19M1 was constructed by Deepak Rajpal by adding BglII, EcoRV, NcoI, and XhoI sites into the multiple cloning region of plasmid pUC19 immediately after the HindIII site. The plasmid vector PCR-Script was obtained from Stratagene. The E. coli strains XL1-Blue MRF' and XLOLR were purchased from Stratagene. The yeast strain CL1265rev1Δ (MATα rev1Δ arg4-17 leu2-3,112 his3-Δ1 trp ura3-52) was derived from CL1265-7C (1) by deleting the REV1 gene.

Isolation of Human REV1 cDNA

Based on a human EST sequence (GenBank accession number AA029147), a 59-mer oligonucleotide (probe I), CATGGTACGAAAGCCTGGGGTCCTGTA-GAAACTGCAAAATTTGGAGGCCATGGAATTTG (SEQ ID NO:1), was synthesized. After labeling with $^{32}$P at its 5' end by T4 polynucleotide kinase, the probe was used to screen human bone marrow and leukocyte cDNA libraries by plaque DNA hybridization (23). Seventeen positive clones were isolated from approximately 1.6 million independent clones. Each insert cDNA was either directly subcloned into the EcoRI site of pUC19 plasmid vector or amplified by PCR prior to plasmid subcloning using the λ phage-derived primers, CGGCAGTACAATGGATTTCCTT (SEQ ID NO:2) and CATCGCCATCTGCTGCAC (SEQ ID NO:3). These cDNA inserts were sequenced by the standard dideoxynucleotide chain termination method on both strands. The overlapping cDNA sequences yielded a partial cDNA sequence of 4.2 kb. Based on the 5' region of this sequence, two 59-mer oligonucleotides, CATTAGTTTTCT-CAATCTCAGCGGAAGATCTGTGTATC-CATTAACATAGATGGCAACTC (SEQ ID NO:4) (probes II) and CCACCCCATGTTTTCCAGCCAT-CATTTTCAGCTCGCTTCCTCCATCCAC-CTCGCCTCAT (SEQ ID NO:5) (probe III), were synthesized and used to screen a human T cell cDNA library. Approximately 40 cDNA clones were isolated and their insert sequences determined. Additional 5' sequence of the human REV1 cDNA was obtained from some clones. Combining the 5' and 3' sequences of various cDNA clones, the complete sequence of a 4,255-bp human REV1 cDNA was generated.

Construction of a Full-length Human REV1 cDNA

The insert cDNA from two λgt11 clones with overlapping partial human REV1 cDNA sequences were excised from the phage DNA with SalI restriction endonuclease and subcloned into the plasmid vector pUC19M1. The resulting plasmids, pWL269 and pWL270, contain the 3' half and the 5' half of the human REV1 cDNA, respectively. The full-length human REV1 cDNA was constructed by ligating a 1.7 kb XbaI-SphI fragment from pWL270 and a 2.7 kb SphI-SacI fragment from pWL269 into the SacI-XbaI sites of the plasmid vector pUC19. The resulting recombinant plasmid, pWL296, contained the full-length human REV1 cDNA.

Isolation of Human REV1 Genomic Clones

A human REV1 clone from the human T cell cDNA library was excised in vivo from the ZAP Express vector in E. coli XL1-Blue MRF' cells infected with a M13 helper phage. The resulting packaged phagemid particles were used to infect E. coli XLOLR cells to convert the phagemid into a double-stranded plasmid containing the human REV1 cDNA. The recovered plasmid was then digested with EcoRI restriction endonuclease, releasing the 0.8 kb human REV1 cDNA insert (corresponding to the human REV1 cDNA position −178 to +646) from the plasmid vector. After isolating it from an agarose gel, this cDNA fragment was used as the template to prepare $^{32}$P-labeled DNA probes by randomly primed DNA synthesis. Approximately 2 million clones from a human placenta genomic DNA library were screened with the human REV1 probes. Two clones were isolated. The DNA inserts of approximately 20 kb each were subcloned into the NotI site of PCR-Script vector and partially sequenced.

Northern Blot Analysis of the Human REV1 mRNA

A 59-mer oligonucleotide probe, corresponding to the human REV1 cDNA position −126 to −184, was synthesized and labeled with $^{32}$P at its 5' end by T4 polynucleotide kinase. A human mRNA blot (Invitrogen) was hybridized with the probe in a buffer containing 50% formamide, 0.25 M NaCl, 0.25 M sodium phosphate, pH 7.2, 1 mM EDTA, and 5% SDS at 42° C. for 18 h. The blot was washed with 15 mM NaCl, 1 mM sodium phosphate, pH7.4, and 0.1 mM EDTA at 60° C. for 1 h. The hybridized human REV1 mRNA was visualized by autoradiography at −80° C. with an intensifying screen.

Detection of the Human REV1 Expression

Expression of the REV1 gene in various human tissues was detected by RT-PCR. Poly(A) mRNA samples were isolated from various human tissues and used for first strand cDNA synthesis by reverse transcriptase. These cDNA samples were then normalized against glyceraldehyde-3-phosphate dehydrogenase cDNA. Such human multiple tissue cDNA panels were purchased from Clontech Laboratories and used for PCR. Two PCR primers, CCCAGGAGGAGGATAAGGCTG (SEQ ID NO:6) and GTCTTTGTAGGGTATTGACAAACTCAGTC (SEQ ID NO:7), were used to amplify a 360 bp region of the human REV1 cDNA. PCR reactions (20 μl) contained 0.4 ng cDNA, 5 pmol each of the primers, 2 mM $MgCl_2$, 20 mM Tris-HCl, pH8.0, 50 mM KCl, 200 μM each of dATP, dCTP, dGTP, and dTTP, and 1 unit of Taq DNA polymerase. After heating at 94° C. for 30 sec, 35 cycles of amplification were performed according to the following conditions: 20 sec denaturation at 94° C., 30 sec annealing at 60° C., and 45 sec extension at 68° C. Reaction products were separated by electrophoresis on a 1% agarose gel containing 0.5 μg/ml ethidium bromide.

Purification of the Human REV1 Protein

The 5' 2.3 kb open reading frame of the human REV1 cDNA was amplified from pWL296 by PCR, generating a DNA fragment flanked by XbaI (added by the 5' PCR primer) and HindIII sites. This DNA fragment was cloned into the XbaI-HindIII sites of the yeast expression vector pEGLh6 (24). At its HindIII site, a 2 kb HindIII DNA fragment containing the missing 3' end of the human REV1 was then transferred from pWL296. The resulting plasmid pEGLh6-hREV1 codes for the full-length human REV1 protein tagged with 6 histidine residues at its N-terminus.

A yeast rev1 delta deletion mutant strain was transformed with pEGLh6-hREV1 for regulated human REV1 expression under the control of the GAL1/10 promoter. Yeast cells containing pEGLh6-hREV1 were grown in minimum medium containing 2% sucrose to late logarithmic phase. Expression of the human REV1 was induced by diluting the culture 10-fold in 16 L of YPG (2% Bacto-peptone, 1% yeast extract, and 2% galactose) medium supplemented with sucrose to a final concentration of 0.5% and growth for 16 h at 30° C. Cells were collected by centrifugation at 6,000×g for 10 min at 4° C. and washed in water. After resuspending in an extraction buffer containing 50 mM Tris-HCl, pH7.5, 600 mM KCl, 10% sucrose, 5 mM β-mercaptoethanol, and protease inhibitors (25), cells were homogenized by Zirconium beads in a Bead-beater (BioSpec Products) for 15 pulses of 30 sec each. The clarified extract (~100 ml) was loaded onto a $Ni^{2+}$-Sepharose column (10 ml) (Amersham Pharmacia Biotech), followed by washing the column with 100 ml of Ni buffer A (20 mM potassium phosphate, pH7.2, 0.5 M NaCl, 20 mM imidazole, 10% glycerol, 5 mM β-mercaptoethanol and protease inhibitors). Bound proteins were eluted with a linear gradient of 20 mM to 135 mM imidazole (100 ml). The REV1 protein fractions were identified by Western blots using a monoclonal anti-His antibody (Qiagene) and pooled. NaCl in the human REV1 sample was replaced with 50 mM KCl by passing the sample through a G-25 Sephadex column. Some protein precipitates were formed, which contained a significant amount of the human REV1 protein. The protein precipitates were recovered by centrifugation at 20,000×g for 10 min at 4° C. and dissolved in a buffer containing 20 mM potassium phosphate, pH7.2, 1 M KCl, 10% glycerol, and 5 mM β-mercaptoethanol. This sample containing partially purified hREV1 was used for some activity assays. To further purify the human REV1 protein, the soluble fraction from the G-25 Sephadex column was loaded onto a FPLC Mono S HR 5/5 column (Amersham Pharmacia Biotech) that had been equilibrated in P buffer (20 mM $KH_2PO_4$, pH7.4, 1 mM EDTA, 5 mM B-mercaptoethanol, 10% glycerol, and protease inhibitors) containing 50 mM KCl. The column was eluted with a linear KCl gradient from 50 mM to 500 mM in P buffer. The human REV1 eluted at ~190 mM KCl. The KCl concentration in the combined Mono S fractions were reduced to 50 mM by gel filtration through a G-25 Sephadex column, and subsequently loaded onto a FPLC Mono Q HR 5/5 column (Amersham Pharmacia Biotech). Column equilibration and elution conditions were as in the Mono S chromatography. The most pure human REV1 eluted at ~320 mM KCl.

Deoxycytidyl Transferase Assay

Deoxycytidyl transferase assays were performed essentially as described by Nelson et al. (15). The reaction mixture (10 μl) contained 25 mM potassium phosphate buffer, pH 7.4, 5 mM $MgCl_2$, 0.1 mg/ml BSA, 10% glycerol, 5 mM dithiothreitol, 100 μM dNTP (dATP, dCTP, dGTP, dTTP, or all four), 20 nM of 5' end $^{32}$P-labeled oligonucleotide primer annealed to an oligonucleotide template as indicated, and protein sample. After incubation at 30° C. for 30 min, reactions were terminated with 7 μl of stop solution (20 mM EDTA, 95% formamide, 0.05% bromophenol blue, and 0.05% xylene cyanol). The reaction products were resolved on a 12% polyacrylamide gel containing 8 M urea and visualized by autoradiography. To obtain DNA substrate containing an abasic site, the uracil-containing substrate (10 pmol) was treated with 2 units of E. coli uracil-DNA glycosylase at 37° C. for 60 min. Under this condition, the site-specific uracil residue was converted to an AP site in the template.

Results

Cloning of the Human REV1 cDNA

Using the yeast Rev1 protein sequence, the non-redundant GenBank CDS database was searched for its homologues. A C. elegans hypothetical protein (ZK675.2) was identified. Alignment of 710 amino acid residues showed 27% identity and 44% similarity to the yeast Rev1. Thus, this C. elegans protein is a homologue of the yeast Rev1. Using the C. elegans REV1 protein sequence, the GenBank EST (expressed sequence tag) database was subsequently searched and a human EST clone (GenBank accession number AA029147) was identified. Based on this clone, the EST database was searched again and two related EST clones (GenBank accession numbers AA393888 and T08134) were identified. Combining the three EST sequences, a partial 3' cDNA sequence of the putative human REV1 gene was obtained.

To isolate the full-length human REV1 cDNA, a 59-mer oligonucleotide probe was synthesized and three human cDNA libraries were screened. As a result, an additional 5' sequence of the putative human REV1 gene was obtained. Subsequently, two additional 59-mer oligonucleotide probes were synthesized and used to screen the human cDNA libraries. Forty cDNA clones were isolated, the largest of which contained an insert of 4 kb. The 5' sequence of the putative human REV1 gene was generated after sequencing. Finally, a cDNA clone containing both the 5' and the 3' sequences was reconstructed from partial cDNA clones (GeneBank accession number AF151538). This cDNA (4,255 bp) codes for a protein of 1,251 amino acid residues with a calculated molecular weight of 138,248 Da and pI of 8.76. Upon searching the GenBank with Applicants' protein sequence, the yeast Rev1 was identified as its homologue ($P_N=5\times e^{-36}$). Hence, Applicants' cDNA clone codes for a human homologue of the yeast mutagenesis protein Rev1. Accordingly, this cDNA and its gene is referred to as the human REV1.

Figure 1:
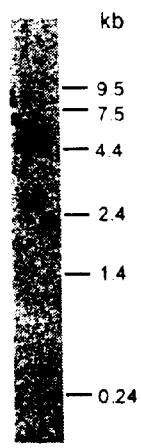
FIG. 1.—Northern blot analysis of the human REV1 mRNA. A RNA sample prepared from normal human heart tissue was separated by electrophoresis and hybridized with a $^{32}$P-labeled 59-mer oligonucleotide probe specific to the human REV1, as described in Materials and Methods. The hybridized human REV1 mRNA was visualized by autoradiography. The RNA size markers in kilobase are indicated on the right.

The sequence context of the putative ATG start codon (CCACCATGA) in Applicants' human REV1 clone matches well with the Kozak consensus sequence (CCACCATGG), which is commonly found surrounding the mammalian ATG initiator codon (26). However, the 5' untranslated region of this human REV1 cDNA does not contain an in-frame termination codon. Furthermore, two cDNA clones contained an intron-like sequence 5' upstream of the position −10, in which the sequence context at the junction closely resembles the consensus sequence of the 3' splicing site. These observations raised the question whether the full-length human REV1 was indeed isolated. To answer this question, the size of the human REV1 mRNA was first determined by a Northern blot analysis. As shown in FIG. 1, the human REV1 mRNA was estimated to be 4.5 kb. This is in good agreement with the size of Applicants' cDNA clone (4.3 kb). Secondly, a human genomic library was screened using the human REV1 cDNA as the probe. Two overlapping genomic clones were isolated. Sequencing these clones confirmed the presence of the 5' splicing site and revealed multiple termination codons upstream of the cDNA sequence (GenBank accession number AF153594). These results show that Applicants have isolated the full-length cDNA of the human REV1. Additionally, the results indicate that the first exon of the human REV1 gene is non-coding.

In the human REV1 cDNA, an out-of-frame ATG codon is located 32 nucleotides upstream of the initiator codon, which could potentially direct the synthesis of a polypeptide of 12 amino acids. Translation from this first ATG codon would lead to an aborted human REV1 protein synthesis. Thus, the translational efficiency of the human REV1 mRNA may be reduced.

Conservation of REV1 Protein Sequences from Yeast to Humans

Figure 2:
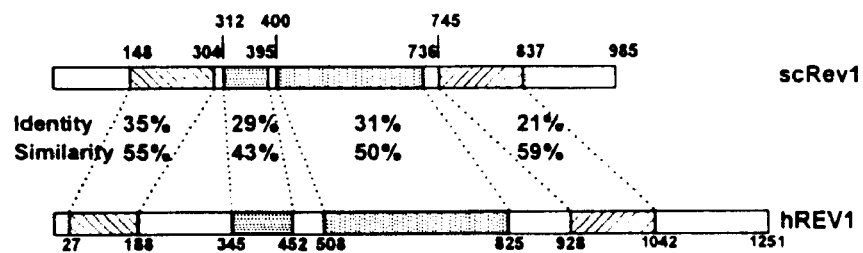
FIG. 2.—Conservation between the yeast and the human REV1 proteins. The yeast and the human REV1 protein sequences were aligned, and the significantly conserved regions of the proteins are schematically indicated by similarly shaded areas. The yeast Rev1 is shown at the top and the human REV1 at the bottom. The amino acid sequence identity and similarity within each conserved region are indicated.

Sequence alignment between the yeast and the human REV1 proteins revealed significant homology (FIG. 2). Four conserved regions were identified with amino acid sequence identities of 21–35% and similarities of 43–59% (FIG. 2). After the human REV1 cDNA was cloned, the A. thaliana and the S. pombe REV1 homologues (GenBank accession numbers AC002342 and AL035548, respectively) were also identified from the genomic sequencing projects. Again, protein sequence conservation was found among these proteins (FIG. 3). Comparison of various REV1 proteins revealed a BRCT (BRCA1 C-terminus) domain at their N-terminal regions and five sequence motifs (FIG. 3).

Chromosomal Localization of the Human REV1 Gene

Using the human REV1 cDNA as the probe, two human REV1 genomic clones were isolated from a library. One clone contained a sequence tagged site (STS), EST164698 (GenBank accession number G25709), upstream from the 5' end of the human REV1 gene. The distance between this STS and the 5' sequence of the human REV1 cDNA was estimated to be 20 kb by PCR using either the genomic clone or the total genomic DNA isolated from human placenta (data not shown). The location of this STS was assigned to 512.6 cR from the top of Chromosome 2 linkage group by Radiation Hybrid Mapping of marker SGC33758 by the Whitehead Institute/MIT Center for Genome Research. On GeneMap'98, it was further mapped to physical position: 355.80 $cR_{3000}$ (P>3.00) between reference intervals D2S113–2S176 (115.3–120.8 cM). These markers are localized between 2q11.1 and 2q11.2 on the cytogenetic ideogram. Therefore, we conclude that the human REV1 gene is located between 2q11.1 and 2q11.2.

Expression of the REV1 Gene in Human Tissues

In yeast, the Rev1-involved mutagenesis pathway is a major mechanism for generating mutations after DNA damage. However, it is not known whether this pathway functions in various human tissues. Thus, the expression of the REV1 gene was examined as an indication of the importance of this putative mutagenesis pathway in various human tissues. As shown in FIG. 4, the human REV1 expression was detected by RT-PCR in all of the 16 tissues examined. Hence, we conclude that the REV1 gene is ubiquitously expressed in humans.

The Human REV1 Protein is a dCMP Transferase

The yeast Rev1 protein possesses a deoxycytidyl transferase activity, which transfers a dCMP residue to the 3' end of a DNA primer opposite a template G or an AP site (15). To determine whether the human REV1 protein is a dCMP transferase, the protein was first partially purified and then the dCMP transferase activity was assayed. To facilitate detection and purification of the human REV1, the protein was tagged with six histidine residues at its N-terminus, and was expressed in yeast rev1 deletion mutant cells. The tagged human REV1 was purified by affinity chromatography on a nickel-Sepharose column. As a control, rev1 deletion mutant extracts were used for identical purification. Using a primed 40-mer DNA template (FIG. 5A), the transferase activity of the partially purified human REV1 was assayed. As shown in FIG. 5B (lane 10), a transferase activity was detected that extended the $^{32}$P-labeled primer by two nucleotides opposite the two template G residues. In contrast, the control sample without the human REV1 did not contain any detectable transferase activity (FIG. 5B, lane 9), indicating that the transferase activity is specific to the human REV1 protein. To identify the nucleotides transferred opposite the template G residues, the transferase assays were performed with dATP, dCTP, dGTP, or dTTP individually, rather than all four dNTPs together. Only dCTP supported the transferase activity (FIG. 5B, lane 4). Again, the transferase activity was not detected with the control sample without the human REV1 protein (FIG. 5B, lanes 1, 3, 5, and 7). The transferase activity was not observed opposite a template A, C, or T (data not shown). Hence, the human REV1 protein is a dCMP transferase, which transfers dCMP opposite a template G. Supporting this conclusion, the transferase activity co-purified with the human REV1 as revealed by Western blots during nickel-Sepharose column chromatography (data not shown). In the control purification from rev1 deletion mutant extracts, none of the fractions contained the transferase activity (data not shown).

To examine whether the transferase activity of the human REV1 functions opposite a template AP site, a site-specific uracil-containing template was prepared (FIG. 6A). Treatment with uracil-DNA glycosylase completely converted the uracil-containing templates into AP site-containing templates, as revealed by the AP site cleavage with the E. coli endonuclease III (FIG. 6B, lane 2). Transferase activity of the human REV1 was detected opposite the template AP site (FIG. 6C, lane 9). A template U also supported the human REV1 transferase activity (FIG. 6C, lane 10). This is also observed with the yeast Rev1 protein (15). However, unlike the yeast protein, which utilizes the template AP site much more efficiently than the template U for its transferase activity (15), the human REV1 uses both the template AP site and uracil efficiently (FIG. 6C, compare lanes 9 and 10). To identify the nucleotides transferred opposite the template AP site or uracil, the transferase assays were performed with only one deoxynucleoside triphosphate, dATP, dCTP, dGTP, or dTTP. As shown in FIG. 6C (lanes 3 and 4), only dCTP supported the human REV1 transferase activity opposite the template AP site or uracil. These results show that the human REV1 protein is a template-dependent dCMP transferase that is active opposite a template G, U, or AP site.

The yeast REV1 gene had been deleted from the host cells used for the human REV1 expression and purification. Thus, the yeast Rev1 could not have contaminated the human REV1 protein preparations. Nevertheless, to provide further support to the conclusion that the human REV1 is a dCMP transferase, the protein was purified to apparent homogeneity (FIGS. 7A and 8B). Again, a transferase activity opposite an AP site was observed with the pure human REV1 preparation (FIG. 7C). Additionally, when the transferase assay was performed opposite a template G using the pure human REV1 protein, the dCMP transferase activity was detected (data not shown). These results show that the observed dCMP transferase activity is associated with the human REV1 protein.

Whereas particular embodiments of this invention have been described above for purposes of illustration, it will be evident to those persons skilled in the art that numerous variations of the details of the present invention may be made without departing from the invention as defined in the appended claims.

All of the references cited herein are incorporated by reference in their entirety.

REFERENCES

1. Morrison, A., Christensen, R. B., Alley, J., Beck, A. K., Bemstine, E. G., Lemontt, J. F. and Lawrence, C. W. (1989) *J. Bacteriol.*, 171, 5659–5667.
2. Lawrence, C. W. and Hinkle, D. C. (1996) *Cancer Surveys*, 28, 21–31.
3. Lawrence, C. (1994) *BioEssays*, 16, 253–258.
4. Lawrence, C. W., Das, G. and Christensen, R. B. (1985) *Mol. Gen. Genet.*, 200, 80–85.
5. Reynolds, P., Weber, S. and Prakash, L. (1985) *Proc. Natl. Acad. Sci. U S A*, 82, 168–172.
6. Jones, J. S., Weber, S. and Prakash, L. (1988) *Nucleic Acids Res.*, 16, 7119–7131.
7. Chanet, R., Magana-Schwencke, N. and Fabre, F. (1988) *Gene*, 74, 543–547.
8. Friedberg, E. C., Walker, G. C. and Siede, W. (1995) DNA Repair and Mutagenesis, American Society of Microbiology Press, Washington, D.C.
9. Jentsch, S., McGrath, J. P. and Varshavsky, A. (1987) *Nature*, 329, 131–134.
10. Bailly, V., Lamb, J., Sung, P., Prakash, S. and Prakash, L. (1994) *Genes Dev.*, 8, 811–820.
11. Bailly, V., Prakash, S. and Prakash, L. (1997) *Mol. Cell. Biol.*, 17, 4536–4543.
12. Bailly, V., Lauder, S., Prakash, S. and Prakash, L. (1997) *J. Biol. Chem.*, 272, 23360–23365.
13. Nelson, J. R., Lawrence, C. W. and Hinkle, D. C. (1996) *Science*, 272, 1646–9.
14. Kulaeva, O. I., Koonin, E. V., McDonald, J. P., Randall, S. K., Rabinovich, N., Connaughton, J. F., Levine, A. S. and Woodgate, R. (1996) *Mutat. Res.*, 357, 245–253.
15. Nelson, J. R., Lawrence, C. W. and Hinkle, D. C. (1996) *Nature*, 382, 729–31.
16. McDonald, J. P., Levine, A. S. and Woodgate, R. (1997) *Genetics*, 147, 1557–1568.
17. Roush, A. A., Suarez, M., Friedberg, E. C., Radman, M. and Siede, W. (1998) *Mol. Gen. Genet.*, 257, 686–692.
18. Johnson, R. E., Prakash, S. and Prakash, L. (1999) *Science*, 283, 1001–4.
19. Koken, M. H. M., Smit, E. M. E., Jaspers-Dekker, I., Oostra, B. A., Hagemeijer, A., Bootsma, D. and Hoeijmakers, J. H. J. (1992) *Genomics*, 12, 447–453.
20. Koken, M. H. M., Reynolds, P., Jaspers-Dekker, I., Prakash, L., Prakash, S., Bootsma, D. and Hoeijmakers, J. H. J. (1991) *Proc. Natl. Acad. Sci. USA*, 88, 8865–8869.
21. Gibbs, P. E., McGregor, W. G., Maher, V. M., Nisson, P. and Lawrence, C. W. (1998) *Proc. Natl. Acad. Sci. USA*, 95, 6876–6880.
22. Lin, W., Wu, X. and Wang, Z. (1999) *Mutat. Res.*, 433, 89–98.
23. Sambrook, J., Fritsch, E. F. and Maniatis, T. (1989) Molecular Cloning: A Laboratory Manual, 2nd Edition Ed., Cold Spring Harbor Laboratory Press, Cold Spring Harbor.
24. Wu, X., Braithwaite, E. and Wang, Z. (1999) *Biochemistry*, 38, 2628–2635.
25. Wang, Z., Wu, X. and Friedberg, E. C. (1995) *Methods*, 7, 177–186.
26. Kozak, M. (1987) *Nucleic Acids Res.*, 15, 8125–8148.
27. Larimer, F. W., Perry, J. R. and Hardigree, A. A. (1989) *J. Bacteriol.*, 171, 230–237.
28. Koonin, E. V., Altschul, S. F. and Bork, P. (1996) *Nature Genet.*, 13, 266–268.
29. Callebaut, I. and Mornon, J. P. (1997) *FEBS Lett.*, 400, 25–30.
30. Bork, P., Hofmann, K., Bucher, P., Neuwald, A. F., Altschul, S. F. and Koonin, E. V. (1997) *FASEB J.*, 11, 68–76.
31. Zhang, X., Morera, S., Bates, P. A., Whitehead, P. C., Coffer, A. I., Hainbucher, K., Nash, R. A., Sternberg, M. J., Lindahl, T. and Freemont, P. S. (1998) *EMBO J.*, 17, 6404–6411.
32. Wixler, V., Laplantine, E., Geerts, D., Sonnenberg, A., Petersohn, D., Eckes, B., Paulsson, M. and Aumailley, M. (1999) *FEBS Lett.*, 445, 351–355.
33. Johnson, R. E., Torres-Ramos, C. A., Izumi, T., Mitra, S., Prakash, S. and Prakash, L. (1998) *Genes. Dev.*, 12, 3137–3143.

TABLE 1

```
                                                                                gcggagcgcgcgcggggttggtt
203[181]
gccgcgagcgtgggggagcgtggaccgcggcgctgctcagcggtggggctgccttcccccggccctcctccctggtccctggcgagggca              -91
ctggcggcggcggggccggggtccgcaaggccggagaaggccgcgggccgggcatggtggtctggggcaacgcggaagaagctccacc              -1
ATGAGGCGAGGTGGATGGAGGAAGCGAGCTGAAAATGATGGCTGGGAAACATGGGGTGGGTATATGGCTGCCAAGGTCCAGAAATTGGAG              90
 M  R  R  G  W  R  K  R  A  E  N  D  G  W  E  T  W  G  G  Y  M  A  A  K  V  Q  K  L  E                 30
GAACAGTTTCGATCAGATGCTGCTATGCAGAAGGATGGGACTTCATCTACAATTTTTAGTGGAGTTGCCATCTATGTTAATGGATACACA              180
 E  Q  F  R  S  D  A  A  M  Q  K  D  G  T  S  S  T  I  F  S  G  V  A  I  Y  V  N  G  Y  T              60
GATCCTTCCGCTGAGGAATTGAGAAAACTAATGATGTTGCATGGAGGTCAATACCATGTATATTATTCCAGATCTAAAACAACACATATT              270
 D  P  S  A  E  E  L  R  K  L  M  M  L  H  G  G  Q  Y  H  V  Y  Y  S  R  S  K  T  T  H  I              90
ATTGCCACAAATCTTCCCAATGCCAAAATTAAAGAATTAAAGGGGGAAAAAGTAATTCGACCAGAATGGATTGTGGAAAGCATCAAAGCT              360
 I  A  T  N  L  P  N  A  K  I  K  E  L  K  G  E  K  V  I  R  P  E  W  I  V  E  S  I  K  A              120
GGACGACTCCTCTCCTACATTCCATATCAGCTGTACACCAAGCAGTCCAGTGTGCAGAAAGGTCTCAGCTTTAATCCTGTATGCAGACCT              450
 G  R  L  L  S  Y  I  P  Y  Q  L  Y  T  K  Q  S  S  V  Q  K  G  L  S  F  N  P  V  C  R  P              150
GAGGATCCTCTGCCAGGTCCAAGCAATATAGCCAAACAGCTCAACAACAGGGTAAATCACATCGTTAAGAAGATTGAAACGGAAAATGAA              540
 E  D  P  L  P  G  P  S  N  I  A  K  Q  L  N  N  R  V  N  H  I  V  K  K  I  E  T  E  N  E              180
GTCAAAGTCAATGGCATGAACAGTTGGAATGAAGAAGATGAAAATAATGATTTTAGTTTTGTGGATCTGGAGCAGACCTCTCCGGGAAGG              630
 V  K  V  N  G  M  N  S  W  N  E  E  D  E  N  N  D  F  S  F  V  D  L  E  Q  T  S  P  G  R              210
AAACAGAATGGAATTCCGCATCCCAGAGGGAGCACTGCCATTTTTAATGGACACACTCCTAGCTCTAATGGTGCCTTAAAGACACAGGAT              720
 K  Q  N  G  I  P  H  P  R  G  S  T  A  I  F  N  G  H  T  P  S  S  N  G  A  L  K  T  Q  D              240
TGCTTGGTGCCCATGGTCAACAGTGTTGCCAGCAGGCTTTCTCCAGCCTTTTCCCAGGAGGAGGATAAGGCTGAGAAGAGCAGCACTGAT              810
 C  L  V  P  M  V  N  S  V  A  S  R  L  S  P  A  F  S  Q  E  E  D  K  A  E  K  S  S  T  D              270
TTCAGAGACTGCACTCTGCAGCAGTTGCAGCAAAGCACCAGAAACACAGATGCTTTGCGGAATCCACACAGAACTAATTCTTTCTCATTA              900
 F  R  D  C  T  L  Q  Q  L  Q  Q  S  T  R  N  T  D  A  L  R  N  P  H  R  T  N  S  F  S  L              300
TCACCTTTGCACAGTAACACTAAAATCAATGGTGCTCACCACTCCACTGTTCAGGGGCCTTCAAGCACAAAAAGCACTTCTTCAGTATCT              990
 S  P  L  H  S  N  T  K  I  N  G  A  H  H  S  T  V  Q  G  P  S  S  T  K  S  T  S  S  V  S              330
ACGTTTAGCAAGGCAGCACCTTCAGTGCCATCCAAACCTTCAGACTGCAATTTTATTTCAAACTTCTATTCTCATTCAAGACTGCATCAC              1080
```

TABLE 1-continued

```
 T  F  S  K  A  A  P  S  V  P  S  K  P  S  D  C  N  F  I  S  N  F  Y  S  H  S  R  L  H  H           360
ATATCAATGTGGAAGTGTGAATTGACTGAGTTTGTCAATACCCTACAAAGACAAAGTAATGGTATCTTTCCAGGAAGGGAAAAGTTAAAA         1170
 I  S  M  W  K  C  E  L  T  E  F  V  N  T  L  Q  R  Q  S  N  G  I  F  P  G  R  E  K  L  K           390
AAAATGAAAACAGGCAGGTCTGCACTTGTTGTAACTGACACAGGAGATATGTCAGTATTGAATTCTCCCAGACATCAGAGCTGTATAATG         1260
 K  M  K  T  G  R  S  A  L  V  V  T  D  T  G  D  M  S  V  L  N  S  P  R  H  Q  S  C  I  M           420
CATGTTGATATGGATTGCTTCTTTGTATCAGTGGGTATACGAAATAGACCAGATCTCAAAGGAAAACCAGTGGCTGTTACAAGTAACAGA         1350
 H  V  D  M  D  C  F  F  V  S  V  G  I  R  N  R  P  D  L  K  G  K  P  V  A  V  T  S  N  R           450
GGCACAGGAAGGGCACCTTTACGTCCTGGCGCTAACCCCAGCTGGAGTGGCAGTATTACCAGAATAAAATCCTGAAAGGCAAAGCAGCA         1440
 G  T  G  R  A  P  L  R  P  G  A  N  P  Q  L  E  W  Q  Y  Y  Q  N  K  I  L  K  G  K  A  A           480
GATATACCAGATTCATCATTGTGGGAGAATCCAGATTCTGCGCAAGCAAATGGAATTGATTCTGTTTTGTCAAGGGCTGAAATTGCATCT         1530
 D  I  P  D  S  S  L  W  E  N  P  D  S  A  Q  A  N  G  I  D  S  V  L  S  R  A  E  I  A  S           510
TGTAGTTATGAGGCCAGGCAACTTGGCATTAAGAACGGAATGTTTTTTGGGCATGCTAAACAACTATGTCCTAATCTTCAAGCTGTTCCA         1620
 C  S  Y  E  A  R  Q  L  G  I  K  N  G  M  F  F  G  H  A  K  Q  L  C  P  N  L  Q  A  V  P           540
TACGATTTTCATGCATATAAGGAAGTCGCACAAACATTGTATGAAACATTGGCAAGCTACACTCATAACATTGAAGCTGTCAGTTGTGAT         1710
 Y  D  F  H  A  Y  K  E  V  A  Q  T  L  Y  E  T  L  A  S  Y  T  H  N  I  E  A  V  S  C  D           570
GAAGCGCTGGTAGACATTACCGAAATCCTTGCAGAGACCAAACTTACTCCTGATGAATTTGCAAATGCTGTTCGTATGGAAATCAAAGAC         1800
 E  A  L  V  D  I  T  E  I  L  A  E  T  K  L  T  P  D  E  F  A  N  A  V  R  M  E  I  K  D           600
CAGACGAAATGTGCTGCCTCTGTTGGAATTGGTTCTAATATTCTCCTGGCTAGAATGGCAACTAGAAAAGCAAAACCAGATGGGCAGTAC         1890
 Q  T  K  C  A  A  S  V  G  I  G  S  N  I  L  L  A  R  M  A  T  R  K  A  K  P  D  G  Q  Y           630
CACCTAAAACCAGAAGAAGTAGATGATTTTATCAGAGGCCAGCTAGTGACCAATCTACCAGGAGTTGGACATTCAATGGAATCTAAGTTG         1980
 H  L  K  P  E  E  V  D  D  F  I  R  G  Q  L  V  T  N  L  P  G  V  G  H  S  M  E  S  K  L           660
GCATCTTTGGGAATTAAAACTTGTGGAGACTTGCAGTATATGACCATGGCAAAACTCCAAAAAGAATTTGGTCCCAAAACAGGTCAGATG         2070
 A  S  L  G  I  K  T  C  G  D  L  Q  Y  M  T  M  A  K  L  Q  K  E  F  G  P  K  T  G  Q  M           690
CTTTATAGGTTCTGCCGTGGCTTGGATGATAGACCAGTTCGAACTGAAAAGGAAAGAAAATCTGTTTCAGCTGAGATCAACTATGGAATA         2160
 L  Y  R  F  C  R  G  L  D  D  R  P  V  R  T  E  K  E  R  K  S  V  S  A  E  I  N  Y  G  I           720
AGGTTTACTCAGCCAAAAGAGGCAGAAGCTTTTCTTCTGAGTCTTTCAGAAGAAATTCAAAGAAGACTAGAAGCCACTGGCATGAAGGGT         2250
 R  F  T  Q  P  K  E  A  E  A  F  L  L  S  L  S  E  E  I  Q  R  R  L  E  A  T  G  M  K  G           750
AAACGTCTAACTCTCAAAATCATGGTACGAAAGCCTGGGGCTCCTGTAGAAACTGCAAAATTTGGAGGCCATGGAATTTGTGATAACATT         2340
 K  R  L  T  L  K  I  M  V  R  K  P  G  A  P  V  E  T  A  K  F  G  G  H  G  I  C  D  N  I           780
GCCAGGACTGTAACTCTTGACCAGGCAACAGATAATGCAAAAATAATTGGAAAGGCGATGCTAAACATGTTTCATACAATGAAACTAAAT         2430
 A  R  T  V  T  L  D  Q  A  T  D  N  A  K  I  I  G  K  A  M  L  N  M  F  H  T  M  K  L  N           810
ATATCAGATATGAGAGGGGTTGGGATTCACGTGAATCAGTTGGTTCCAACTAATCTGAACCCTTCCACATGTCCCAGTCGCCCATCAGTT         2520
 I  S  D  M  R  G  V  G  I  H  V  N  Q  L  V  P  T  N  L  N  P  S  T  C  P  S  R  P  S  V           840
CAGTCAAGCCACTTTCCTAGTGGGTCATACTCTGTCCGTGATGTCTTCCAAGTTCAGAAAGCTAAGAAATCCACCGAAGAGGAGCACAAA         2610
 Q  S  S  H  F  P  S  G  S  Y  S  V  R  D  V  F  Q  V  Q  K  A  K  K  S  T  E  E  E  H  K           870
GAAGTATTTCGGGCTGCTGTGGATCTGGAAATATCATCTGCTTCTAGAACTTGCACTTTCTTGCCACCTTTTCCTGCACATCTGCCGACC         2700
 E  V  F  R  A  A  V  D  L  E  I  S  S  A  S  R  T  C  T  F  L  P  P  F  P  A  H  L  P  T           900
AGTCCTGATACTAACAAGGCTGAGTCTTCAGGGAAATGGAATGGTCTACATACTCCTGTCAGTGTGCAGTCGAGACTTAACCTGAGTATA         2790
 S  P  D  T  N  K  A  E  S  S  G  K  W  N  G  L  H  T  P  V  S  V  Q  S  R  L  N  L  S  I           930
GAGGTCCCGTCACCTTCCCAGCTGGATCAGTCTGTTTTAGAAGCACTTCCACCTGATCTCCGGGAACAAGTAGAGCAAGTCTGTGCTGTC         2880
 E  V  P  S  P  S  Q  L  D  Q  S  V  L  E  A  L  P  P  D  L  R  E  Q  V  E  Q  V  C  A  V           960
CAGCAAGCAGAGTCACATGGCGACAAAAAGAAAGAACCAGTAAATGGCTGTAATACAGGAATTTTGCCACAACCAGTTGGGACAGTCTTG         2970
 Q  Q  A  E  S  H  G  D  K  K  K  E  P  V  N  G  C  N  T  G  I  L  P  Q  P  V  G  T  V  L           990
TTGCAAATACCAGAACCTCAAGAATCGAACAGTGACGCAGGAATAAATTTAATAGCCCTTCCAGCATTTTCACAGGTGGACCCTGAGGTA         3060
 L  Q  I  P  E  P  Q  E  S  N  S  D  A  G  I  N  L  I  A  L  P  A  F  S  Q  V  D  P  E  V          1020
TTTGCTGCCCTTCCTGCTGAACTTCAGAGGGAGCTGAAAGCAGCGTATGATCAAAGACAAAGGCAGGGCGAGAACAGCACTCACCAGCAG         3150
 F  A  A  L  P  A  E  L  Q  R  E  L  K  A  A  Y  D  Q  R  Q  R  Q  G  E  N  S  T  H  Q  Q          1050
TCAGCCAGCGCATCTGTCCAAAGAATCCTTTACTTCATCTAAAGGCAGCAGTGAAAGAAAAGAAAAGAAAACAAGAAGAAAAACCATC         3240
 S  A  S  A  S  V  P  K  N  P  L  L  H  L  K  A  A  V  K  E  K  K  R  N  K  K  K  K  T  I          1080
GGTTCACCAAAAAGGATTCAGAGTCCTTTGAATAACAAGCTGCTTAACAGTCCTGCAAAAACTCTGCCAGGGCCTGTGGCAGTCCCCAG         3330
 G  S  P  K  R  I  Q  S  P  L  N  N  K  L  L  N  S  P  A  K  T  L  P  G  A  C  G  S  P  Q          1110
AAGTTAATTGATGGTTTCTAAAACATGAAGGACCTCCTGCAGAGAAACCCCTGAAGAACTCTCTGCTTCTACTTCAGGTGTGCCAGGC         3420
 K  L  I  D  G  F  L  K  H  E  G  P  P  A  E  K  P  L  E  E  L  S  A  S  T  S  G  V  P  G          1140
CTTTCTAGTTTGCAGTCTGACCCAGCTGGCTGTGTGAGACCTCCAGCACCCAATCTAGCTGGAGCTGTTGAATTCAATGATGTGAAGACC         3510
 L  S  S  L  Q  S  D  P  A  G  C  V  R  P  P  A  P  N  L  A  G  A  V  E  F  N  D  V  K  T          1170
TTGCTCAGAGAATGGATAACTACAATTTCAGATCCAATGGAAGAAGACATTCTCCAAGTTGTGAAATACTGTACTGATCTAATAGAAGAA         3600
 L  L  R  E  W  I  T  T  I  S  D  P  M  E  E  D  I  L  Q  V  V  K  Y  C  T  D  L  I  E  E          1200
AAAGATTTGGAAAAACTGGATCTAGTTATAAAATACATGAAAAGGCTAATGCAGCAATCGGTGGAATCGGTTTGGAATATGGCATTTGAC         3690
 K  D  L  E  K  L  D  L  V  I  K  Y  M  K  R  L  M  Q  Q  S  V  E  S  V  W  N  M  A  F  D          1230
TTTATTCTTGACAATGTCCAGGTGGTTTTACAACAAACTTATGGAAGCACATTAAAAGTTACAtaaatattaccagagagcctgatgctc         3780
 F  I  L  D  N  V  Q  V  V  L  Q  Q  T  Y  G  S  T  L  K  V  T                                      1251
tctgatagctgtgccataagtgcttgtgaggtatttgcaaagtgcatgatagtaatgctcggagttttataattttaaatttctttttaa         3870
agcaagtgttttgtacatttcttttcaaaagtgcccaaatttgtcagtattgcatgtaaataattgtgttaattatttactgtagcata         4960
gattctatttacaaaatgtttgtttataaagttttatggattttttacagtgaagtgtttacagttgtttaataaagaactgtatgtatat         4050
tt                                                                                                 4052
(SEQ ID NO:8 and SEQ ID NO:9)
```

What is claimed is:

1. An isolated nucleic acid molecule comprising a nucleotide sequence encoding the polypeptide of SEQ ID NO:9.

2. The nucleotide sequence of claim 1, which is a DNA.

3. The DNA of claim 2, which comprises a DNA encoding the polypeptide of SEQ ID NO:9.

4. A vector, comprising:
   a replicable vector; and
   the nucleotide sequence of claim 1 inserted into said vector.

5. The vector of claim 4, which is an expression vector capable of expressing said polypeptide.

6. The vector of claim 4, which is a plasmid.

7. An isolated cell containing the vector of claim 4.

* * * * *